United States Patent
Dollar et al.

(10) Patent No.: US 9,788,985 B2
(45) Date of Patent: Oct. 17, 2017

(54) FRICTION-BASED ORTHOTIC IMPEDENCE MODULATION DEVICE

(71) Applicant: Yale University, New Haven, CT (US)

(72) Inventors: Aaron Dollar, New Haven, CT (US); Kamran Shamaei Ghahfarokhi, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 245 days.

(21) Appl. No.: 14/211,246

(22) Filed: Mar. 14, 2014

(65) Prior Publication Data

US 2014/0276304 A1 Sep. 18, 2014

Related U.S. Application Data

(60) Provisional application No. 61/782,769, filed on Mar. 14, 2013.

(51) Int. Cl.
*A61H 3/00* (2006.01)
*A61F 5/01* (2006.01)

(52) U.S. Cl.
CPC .... *A61F 5/0102* (2013.01); *A61F 2005/0169* (2013.01)

(58) Field of Classification Search
CPC .. A61F 5/0102; A61F 2005/0169; A61F 2/60; A61F 2/64; A61F 2/66; A61F 2/604; A61F 5/0123; A61F 5/0125; A61F 5/0127; A61F 5/01; A61H 3/00; A61H 1/02; A61H 1/0262; A61H 2003/001; A61H 1/0255; B25J 9/0006
See application file for complete search history.

(56) References Cited

U.S. PATENT DOCUMENTS

| | | | | |
|---|---|---|---|---|
| 5,311,109 A | * | 5/1994 | Ozawa | B62D 57/032 180/8.1 |
| 5,472,410 A | * | 12/1995 | Hamersly | A61F 5/0125 601/33 |
| 9,221,177 B2 | * | 12/2015 | Herr | B25J 9/1694 |
| 2004/0064195 A1 | * | 4/2004 | Herr | A61F 2/66 623/24 |
| 2005/0070834 A1 | * | 3/2005 | Herr | A61B 5/1038 602/28 |
| 2005/0251079 A1 | * | 11/2005 | Carvey | A61F 5/0102 602/26 |

(Continued)

OTHER PUBLICATIONS

Saunders et al., "Major Determinants in Normal and Pathological Gait," J Bone Joint Surg Am, 35(3): 543-558, 1953.
(Continued)

*Primary Examiner* — Justine Yu
*Assistant Examiner* — Christopher Miller
(74) *Attorney, Agent, or Firm* — Riverside Law LLP

(57) ABSTRACT

The present invention relates to an impedance modulation device for an orthotic application. The device includes a high-stiffness loading spring, a low-stiffness return spring, a shaft having an output connector, and an engagement mechanism. When the engagement mechanism engages the shaft, the device exhibits a high stiffness at the output connector, and wherein when the engagement mechanism disengages the shaft, the device exhibits a low stiffness at the output connector.

12 Claims, 29 Drawing Sheets

(56) References Cited

U.S. PATENT DOCUMENTS

| | | | | |
|---|---|---|---|---|
| 2006/0249315 A1* | 11/2006 | Herr | | A61F 2/60 180/8.1 |
| 2007/0162152 A1* | 7/2007 | Herr | | A61F 2/60 623/24 |
| 2008/0039756 A1* | 2/2008 | Thorsteinsson | | A61B 5/1038 602/23 |
| 2009/0299480 A1* | 12/2009 | Gilbert | | A61F 2/582 623/18.11 |
| 2010/0185301 A1* | 7/2010 | Hansen | | A61F 2/6607 623/47 |
| 2010/0312363 A1* | 12/2010 | Herr | | A61F 2/64 623/39 |
| 2013/0046218 A1* | 2/2013 | Wiggin | | A61F 5/0127 602/16 |
| 2013/0131560 A1* | 5/2013 | Ferguson | | A61H 3/00 601/33 |
| 2013/0296746 A1* | 11/2013 | Herr | | A61H 3/00 601/34 |
| 2014/0100493 A1* | 4/2014 | Craig | | A61H 3/00 601/35 |
| 2014/0296997 A1* | 10/2014 | Herr | | A61F 5/0111 623/24 |

OTHER PUBLICATIONS

Gard et al., "What determines the vertical displacement of the body during normal walking?", J. Prosthet. Orthot, 13(3): 64-67, 2001.

Shamaei et al., "On the Mechanics of the Knee during the Stance Phase of the Gait", IEEE Int Conf Rehabil Robot 2011:5975478, 2011.

Shamaei et al., "On the Mechanics of the Ankle in the Stance Phase of the Gait", Conf Proc IEEE Eng Med Biol Soc, 2011: 8135-8140, 2011.

Shamaei et al., "Estimation of quasistiffness of the human knee in the stance phase of walking", PLoS One, 8(3): e59993, 2013.

Shamaei et al., "A quasi-passive compliant stance control knee-ankle-foot orthosis", Conf Proc. IEEE Int. Conf. Rehabil. Robot, Seattle, WA, 1-6, 2013.

Winter et al., "Joint torque and energy patterns in normal gait", Biological Cybernetics, 29: 137-142, 1978.

Crenna et al., "Dynamics of the ankle joint analyzed through moment-angle loops during human walking: gender and age effects", Human Movement Science, 30: 1185-1198, 2011.

Wiggin et al., "An exoskeleton using controlled energy storage and release to aid ankle propulsion", Conf Proc. IEEE Int. Conf. Rehabil. Robot, Zurich, Switzerland, 1-5, 2011.

Bregman et al., "The effect of ankle foot orthosis stiffness on the energy cost of walking: A simulation study", Clin. Biomechan, 26(9): 955-961, 2011.

Kawamoto et al., "Power assist method based on phase sequence and muscle force condition for HAL", Advanced Robotics, 19(7): 717-734, 2005.

Zoss et al., "On the mechanical design of the Berkeley lower extremity exoskeleton (BLEEX)", Proceedings of IEEE/RSJ International Conference on Intelligent Robots and Systems, 3465-3472, 2005.

* cited by examiner

\* *Engagement depending on the user's impairment level*

Figure 15

| No | Gender | Weight (kg) | Height (cm) | CC Speed (%) | CS Speed (%) | Rs Speed (%) | Stiffness (N/m) |
|---|---|---|---|---|---|---|---|
| 1 | M | 71 | 178 | 1.00 | 1.00 | 1.00 | 2.40 |
| 2 | M | 70 | 170 | 0.90 | 0.90 | 0.75 | 2.40 |
| 3 | M | 74 | 168 | 0.90 | 0.90 | 0.80 | 2.40 |
| Mean | | 73 | 172 | 0.93 | 0.93 | 0.85 | 2.40 |
| SD | | 2.6 | 4 | 0.06 | 0.06 | 0.13 | 0 |

DEMOGRAPHIC DATA OF THE PARTICIPANTS AND TRIALS INFORMATION

Figure 27

FRICTION-BASED ORTHOTIC IMPEDENCE MODULATION DEVICE

CROSS-REFERENCE TO RELATED APPLICATIONS

This application claims priority to U.S. Patent Application Ser. No. 61/782,769 filed Mar. 14, 2013, the entire disclosure of which is incorporated by reference herein in its entirety.

STATEMENT REGARDING FEDERALLY SPONSORED RESEARCH OR DEVELOPMENT

This invention was made with the government support under W81XWH-11-2-0054 awarded by the US Defense Medical Research Development Program. The government has certain rights in the invention.

BACKGROUND OF THE INVENTION

Millions of patients worldwide suffer from hip, knee, and ankle joint disorders, including quadriceps weakness, Patellofemoral Pain Syndrome, or from injuries, stroke, postpolio, multiples sclerosis, or SCI. An improvement in lower extremity assistive devices will benefit some or all of these patients. However, with few exceptions, orthotic options for this population are limited to passive technologies that cannot provide assistance necessary to replicate the function of an unaffected limb. Accordingly, there is great potential for the development of electromechanical devices to drastically increase the quality of life of this population. Gait pathologies and musculoskeletal disorders are often stabilized using a leg orthosis, typically consisting of a crude hard piece of material formed to the wearer's leg. Recently, new orthotic technologies have been introduced that rigidly lock the knee in the stance phase and unlock it in the swing phase of the gait. The rigid support of the knee in the stance phase of the gait results in low gait speed, joint pain due to the absence of shock absorption mechanisms and a pathological gait. The rigid assistance of the ankle highly hinders propulsion and reduces the gait speed.

To overcome these problems, new orthotic technologies require incorporation of compliance tuned based on the gait and subject conditions. Thus, there is a need in the art for a quasi-passive friction-based impedance modulation device for orthotic applications. The present invention satisfies this need.

SUMMARY OF THE INVENTION

An impedance modulation device for an orthotic application is described. The impedance device includes a high-stiffness loading spring, a low-stiffness return spring, a shaft having an output connector, and an engagement mechanism. When the engagement mechanism engages the shaft, the device exhibits a high stiffness at the output connector, and when the engagement mechanism disengages the shaft, the device exhibits a low stiffness at the output connector.

In one embodiment, the engagement mechanism comprises a gear. In another embodiment, the engagement mechanism further comprises an actuator that drives the gear. In another embodiment, the engagement mechanism comprises a lever, wherein the lever is configured to be pushed by the gear. In another embodiment, a portion of the shaft along its length passes through a hole in the lever. In another embodiment, the engagement mechanism engages the shaft by pushing the lever into contact with the shaft. In another embodiment, the engagement mechanism is disengaged from the shaft when the shaft passes easily through the hole in the lever. In another embodiment, at least a portion of the low-stiffness return spring is positioned at least partially within the core of the high-stiffness spring. In another embodiment, at least a portion of the shaft is positioned at least partially within the core of the low-stiffness return spring.

The present invention also includes an orthotic device. The orthotic device includes a frame, an impedance modulator comprising a high-stiffness loading spring, a low-stiffness return spring, a shaft having a connector, and an engagement mechanism, a pulley assembly positioned relative to a joint and connected to the shaft connector, wherein the pulley assembly turns and pulls the shaft of the impedance modulator, and when the engagement mechanism engages the shaft, the modulator exhibits a high stiffness at the shaft connector, and when the engagement mechanism disengages the shaft, the modulator exhibits a low stiffness at the shaft connector.

In one embodiment, the device is a knee-ankle-foot-orthosis. In another embodiment, the orthotic device further includes a controller. In another embodiment, the controller detects if the foot is in contact with the ground or is off the ground, and wherein when the foot is on the ground, the modulator exhibits high stiffness, and when the foot is off the ground, the modulator exhibits low stiffness. In another embodiment, the orthotic device further includes a brushless or brushed motor and a harmonic drive gear.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 15 is a table listing the most general and simplified forms of the statistical models that estimate the knee quasi-stiffness in the weight acceptance phase.

FIG. 27 is a table that includes the demographic data of the volunteers as well as the preferred gait speeds of the trials.

DETAILED DESCRIPTION

Figure 1:
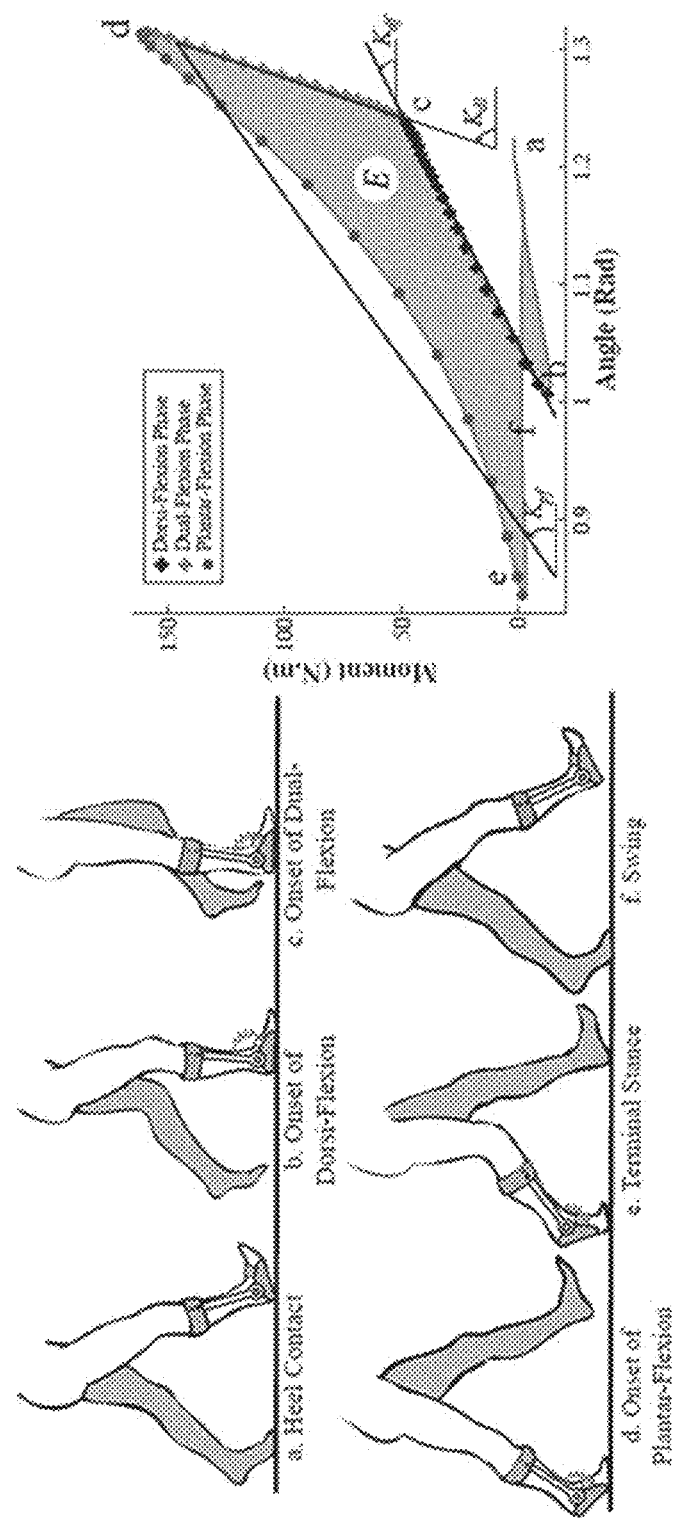
FIG. 1 is a schematic posture of the lower limbs during a gait cycle and the period where the ankle can be stabilized by an orthosis that can introduce external stiffness.

It is to be understood that the figures and descriptions of the present invention have been simplified to illustrate elements that are relevant for a clear understanding of the present invention, while eliminating, for the purpose of clarity, many other elements found in typical orthotic devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

The present invention includes a mechanically simple, quasi-passive friction-based impedance modulation device (quasi-passive compliant stance control) for orthotic applications. The device can function in parallel with the lower extremity joints to introduce a spring that is tuned based on the patient size and gait to replace the function of the impaired joint. In addition to medical orthotic applications, the present invention can also be used as an exoskeletal device to reduce energetic requirements of locomotion for healthy users.

Biomechanical Behavior of the Knee and Ankle

Figure 2:
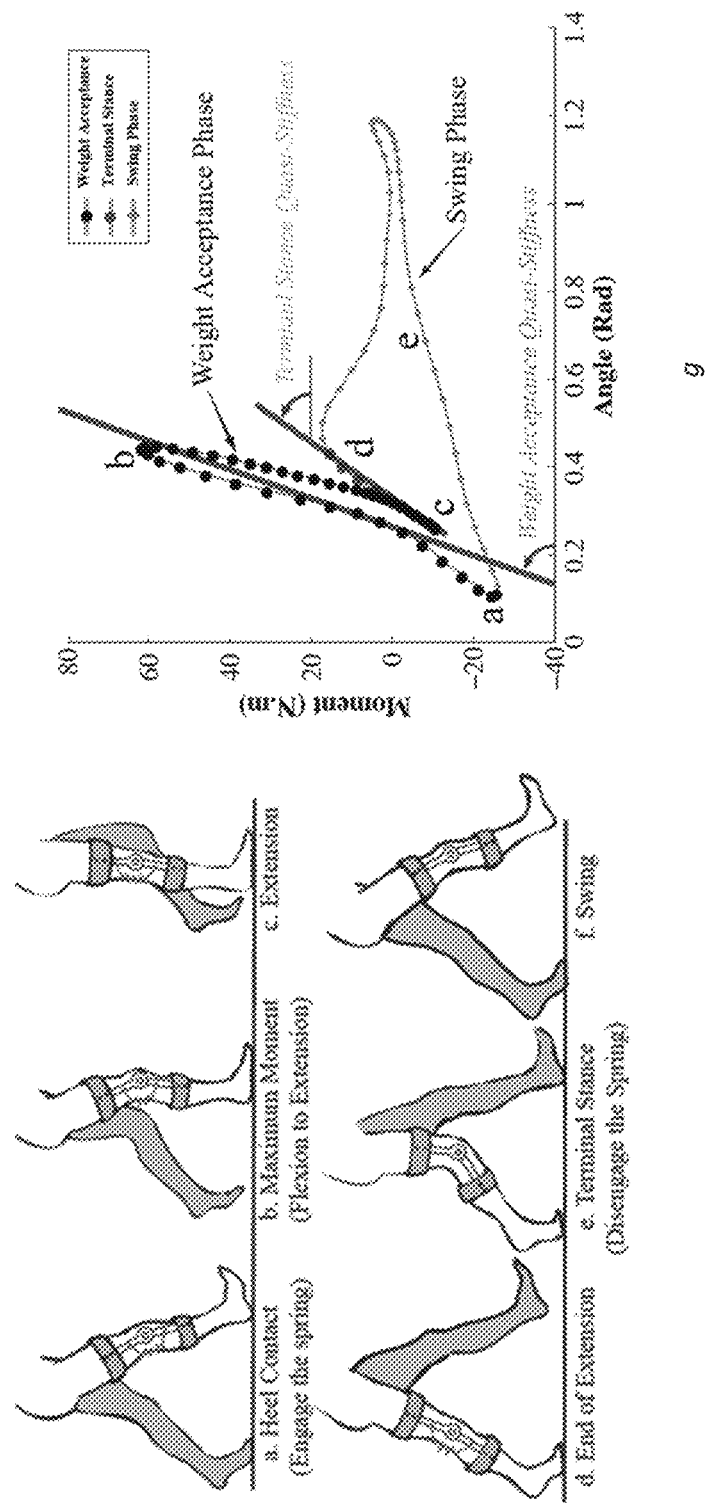
FIG. 2 is a schematic posture of the lower limbs during a gait cycle (a-f) and the period where the knee joint can be stabilized by a compliant stance control orthosis. (g) depicts the moment-angle graph for the knee of a subject walking at 1.25 m·s-1. The slope of the linear fit to the graph in the weight acceptance phase is termed as the knee quasi-stiffness in this phase.

The knee undergoes a flexion in stance which originally was considered a determinant of reduction of travel of the center of gravity [Saunders 1953], and later shown to be a determinant of shock absorption [Gard 2001]. In principle, the knee generates substantial moment in the stance and goes through a relatively silent movement in swing. As a result, the knee is highly prone to collapse in stance and requires compliant stabilization in stance (as an alternative to the available rigid orthoses), and free relatively ballistic movement in swing. Researchers have investigated the moment-angle behavior of the knee and have shown that the knee exhibits linear behavior in the stance phase of the gait, as shown in FIG. 1 [Shamaei 2011a, Shamaei 2013a]. This observation is consistent with the approach that the knee function can be mimicked by a linear torsional spring in the design of orthoses and prostheses during the stance as shown in FIG. 2.

The ankle exhibits an initial plantar-flexion motion within the first about 10% of the gait, as shown in FIGS. 1a and 1b until the foot sole lays on the ground [Perry 1992]. Within the rest of the stance phase, the ankle is primarily involved in the progression of the body [Winter 1978]. The ankle undergoes three sub-phases during the progression period including dorsi-flexion (FIGS. 1b and 1c), dual-flexion (FIGS. 1c and 1d), and plantarflexion (FIGS. 1d and 1e) phases [Crenna 2011, Shamaei 2013b]. Next, the toe leaves the ground and the ankle experiences a relatively silent swing phase (FIGS. 1e and 1f). The dual-flexion phase ends at about 50% of the gait cycle [Crenna 2011, Shamaei 2013b]. The dorsi-flexion and dual-flexion phases separate at about 30% of the stride when the ground reaction force shows a local minimum in the vertical and zero in the horizontal directions [Winter 1991]. Previous studies show that the ankle demonstrate linear behavior in the dorsi-flexion, dual-flexion, and plantar-flexion phases of the stance [Crenna 2011, Shamaei 2011b, Shamaei 2013b].

Based on the biomechanical behavior of the knee and ankle in the stance phase, it is believed that a linear spring in parallel with these joints could help impaired individuals achieve a nearly natural gait [Shamaei 2011a & b] and reduce the energetic demand of the gait [Wiggin 2011, Bregman 2011]. Accordingly, the present invention, demonstrated herein as a quasi-passive variable stiffness knee and ankle orthosis/exoskeleton, can aid with such impairment. As contemplated herein, quasi-passive variable stiffness orthoses may employ clutching mechanisms that switch between different springs and demonstrate a variable stiffness. The present invention may thus be used to engage a spring in parallel with the knee in the weight acceptance phase of the gait as FIG. 2 suggests, and with the ankle in the stance phase of the gait as FIG. 1 suggests.

Figure 3:
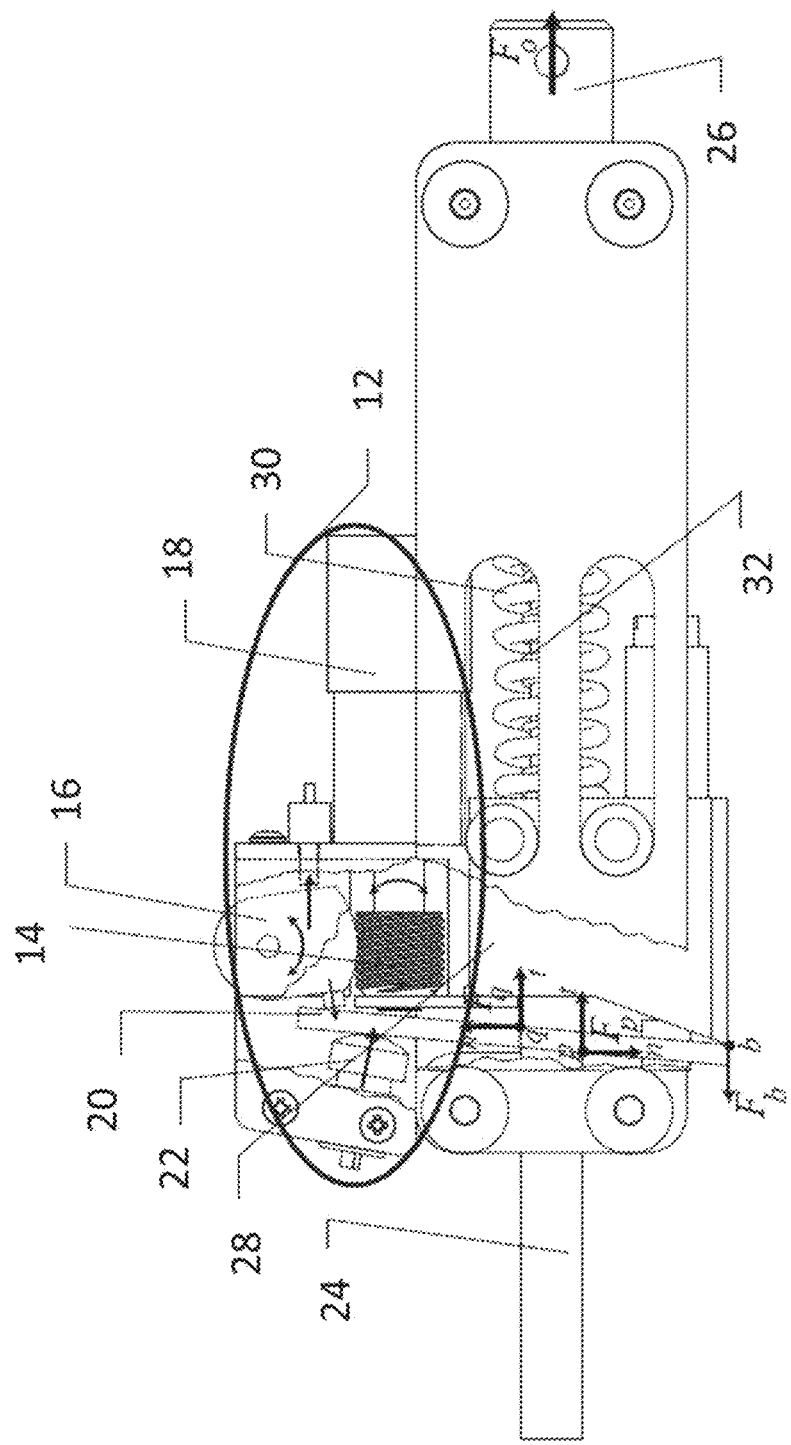
FIG. 3 is a schematic of an exemplary variable stiffness module.

The ankle and knee joints exhibit relatively high quasi-stiffnesses in the stance phase of the gait [Shamaei 2011a & b]. Torsional springs, on the other hand, provide very low stiffness to volume/mass ratio. Thus, assistive devices cannot employ linear torsional springs that provide a stiffness close to the quasi-stiffnesses of the ankle and knee joint and meet the maximum size/weight acceptable for these devices. In one embodiment, the present invention may provide high stiffness while keeping the weight and mass of the system low by using linear die springs. In another embodiment, the present invention includes a friction-based stiffness module that can engage/disengage linear springs and exhibit variable stiffnesses at different periods of the gait as shown in FIG. 3. An exploded view of the stiffness module can be seen in FIG. 4.

Variable Stiffness Module

Figure 5:
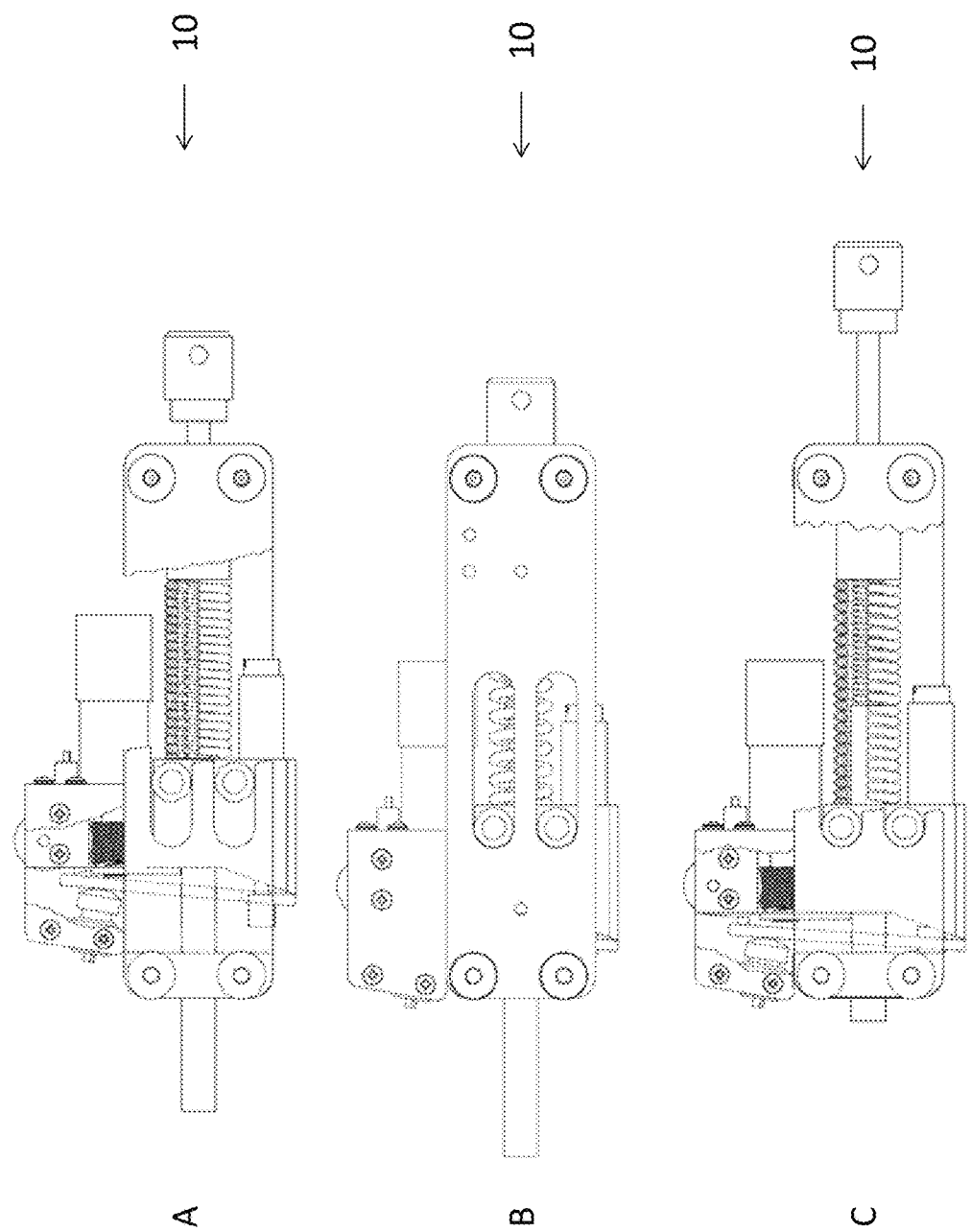
FIG. 5 is a schematic of the variable stiffness module at high stiffness, low stiffness and neutral configurations.

Referring now to FIG. 3, a top view of an exemplary variable stiffness module 10 is shown. An engagement mechanism 12 (circled region) employs a worm-gear set (worm 14, gear 16) that is driven by an actuator, such as a DC motor 18. When DC motor 18 spins clock-wise (CW), gear 16 turns counter clock-wise (CCW) and a friction lever 20 is pushed to the right (when viewed in a landscape page orientation) by a disengagement push-button 22. As a result, friction lever 20 comes in contact with a shaft 24 at two points p and q. If a force is applied at a connector 26, shaft 24 tries to move to right. The friction forces on friction lever 20 at p and q are balanced by the interaction force from a bearing block 28 $F_b$. If the distance between the hole in friction lever 20 to point b is higher than a certain value, the normal components of $F_p''$ and $F_q''$ would be high enough so that friction induces two gripping tangential forces $F_p^t$ and $F_q^t$ at p and q that try to move friction lever 20 to the right. Friction lever 20 in turn, pushes bearing block 28 to the right and against a loading spring 30. As a result, variable stiffness module 10 exhibits the high stiffness of loading spring 30 at the output connector 26 force $F_o$. To disengage, DC motor 18 should spin CCW to move gear 16 to the left and press friction lever 20 against disengagement push-button 22. If friction lever 20 is pushed to the left, it would leave the contact points with shaft 24 and allows shaft 24 to easily move inside the hole of bearing block 28. This compresses a low-stiffness return spring 32 which in turn exhibits low stiffness at the output force $F_o$. A neutral configuration (FIG. 513), as well as high-stiffness (FIG. 5A) and low-stiffness (FIG. 5C) modes of variable stiffness module 10 are shown in FIG. 5.

Accordingly, the present invention may be further characterized as a compliance control module (CCM) that is responsible for engaging and disengaging the support spring in parallel with the knee joint. The CCM exploits friction-based latching to engage the support spring in the stance phase, and disengage it during the rest of the gait. The CCM uses the motor to drive the worm-gear set that, in combination with the spring-loaded push-button, brings the friction lever either in contact with the shaft to latch the bearing block to the shaft, or away from the shaft to unlatch the bearing block and allow for free motion of the shaft inside the bearing block. The engagement mechanism also includes a spring-loaded and a retreat push-button to provide the controller with feedback on the position of the friction lever.

To engage the support spring, the worm-gear should spin counterclockwise to move the gear away from the friction lever and clear behind it. This movement terminates when the gear presses the retreat button, which sends a feedback signal to the controller to stop the motor. The spring-loaded push-button presses the friction lever against the shaft to bring them in contact. This introduces a small friction force on the friction lever at the contact points, which is transferred to the bearing block through the friction lever. The interaction force between the bearing block and the friction lever induces higher normal forces between the friction lever and the shaft, constituting a latching grip between the bearing block, shaft, and friction lever. As such, the bearing block moves along with the shaft and compresses the support spring. Since shaft movement always compresses the return spring, any distal force on the shaft (as a result of knee flexion, compresses both the return and support springs. Consequently, the CCM exhibits the summation of the stiffnesses of both springs along the shaft axis. A proximal force on the shaft (mainly applied by the return spring during knee extension) relaxes the friction forces on the friction lever at the contact points and releases the latching grip. Therefore, a latch only occurs in the flexion direction, and remains if the support spring is engaged and loaded to maintain the latching friction forces.

To disengage the support spring, the worm should spin clockwise to move the gear towards the friction lever. The gear touches the friction lever and releases its latch with the shaft and moves until it presses the spring-loaded push-button after which a feedback signal is sent to the controller to stop the motor. The forces applied on the lever by the gear and spring-loaded button generate a moment-couple that anchors the friction lever on the bearing block. Upon disengagement, the shaft freely slides inside the bearing block and friction lever without any force being transferred to the support spring. Accordingly, a distal force on the shaft only compresses the return spring. To allow free rotation in the swing phase, a relatively slack return spring may be chosen in order to only return the shaft to its original location after the swing phase without applying considerable assistive moment to the knee. The CCM also includes a shock absorber 29 to dissipate any remaining energy, in case the support spring disengages while it is loaded.

Figure 4:
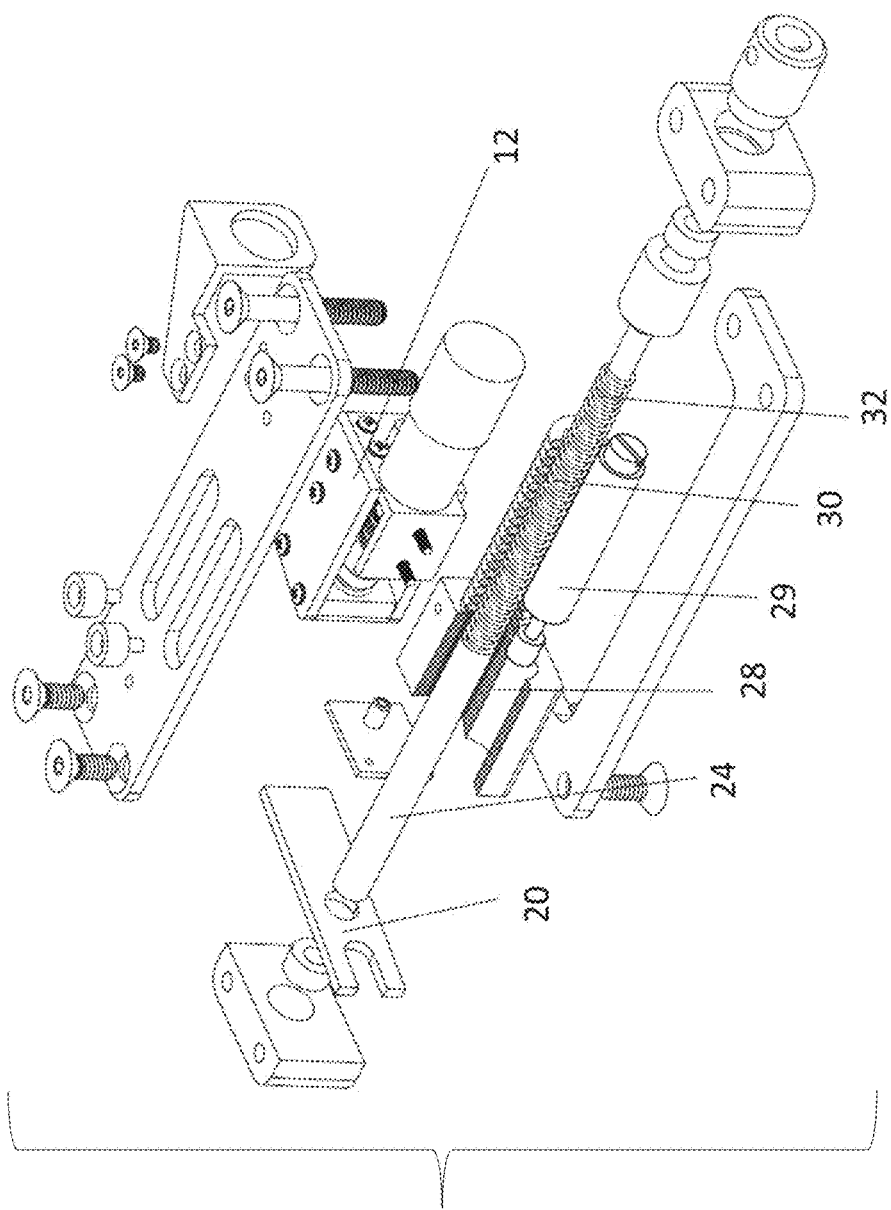
FIG. 4 is an exploded view of the exemplary variable stiffness module of FIG. 3.

While the shaft as illustrated in FIGS. 3-5 is generally linear, it should be appreciated that the shape of the shaft is not limited. Rather, in alternative embodiments, the shaft of the variable stiffness module may have a circular shape, a cam shape, or more generally a curved profile. Further, in certain embodiments the low stiffness or return spring may be replaced by a rigid attachment between the variable stiffness module and any orthotic segments. Additionally, in certain embodiments the orthosis controller can be replaced by a Bowden-cable manipulating the friction lever and being driven by a secondary mechanism according to the leg configuration.

The friction lever 20 is made out of high-speed steel and can be alternatively made with any steel with high hardness. Shaft 24 is made with case hardened steel and can be made with any material that exhibits the required hardness. Engagement motor 18 can be any sort of DC/AC Motor (brushed or brushless), Solenoid, Pizeo-Electric actuator, Pneumatic/Hydraulic actuator, mechanical lever driven by the human or user limbs, or other possible actuators as would be understood by those skilled in the art. Worm 14 is made with hardened steel and gear 16 with brass. The worm/gear set can be alternatively made with any metal that meets the hardness and friction criteria for worm/gear sets. Since the purpose of the worm/gear set driven by DC motor 18 is to engage/disengage friction lever 20 with shaft 24, any other mechanism capable of this linear motion can replace engagement mechanism 10 as could be understood by those skilled in the art. This includes, without limitation, a solenoid, a cam on a geared/ungeared DC motor, linear screw on a DC motor, pneumatic/hydraulic actuator, a mechanism driven by the user limbs, and the like. The variable stiffness module 10 employs a die spring for the high-stiffness (loading) spring 30 and regular compression spring for the low-stiffness return spring 32. The type of springs can be alternatively chosen, provided they demonstrate the range of stiffness required for support of human hip, knee, and ankle.

The controller is implemented on a microcontroller, such as from Freescale Semiconductor Co. (MPC5534EVBE). There is no limitation to the type of controller used, and it should be appreciated that the controller of the present invention can be implemented on any sort of microcontroller capable of driving the device components and processing data as would be understood by those skilled in the art.

Orthoses and Prostheses Applications

Figure 6:
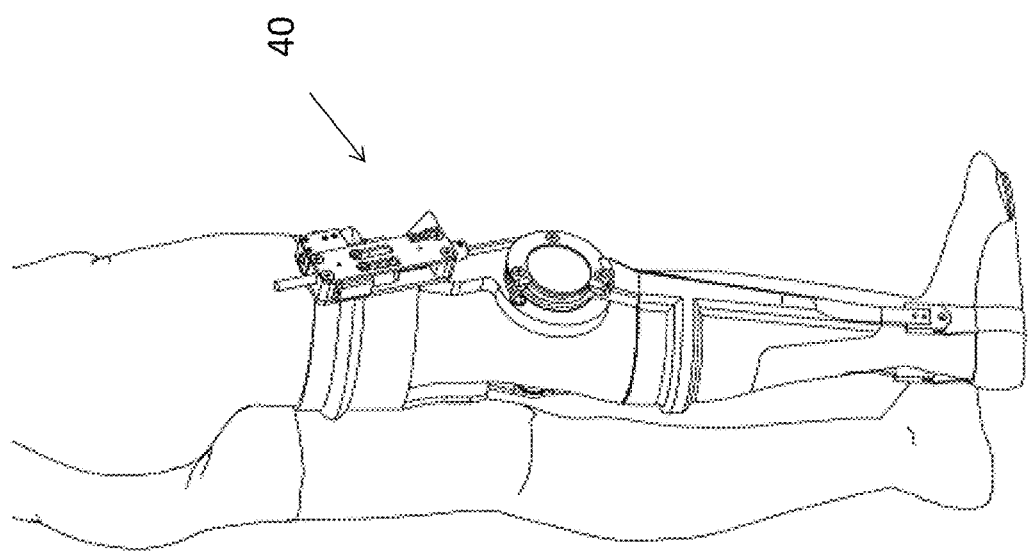
FIG. 6 is a schematic of an exemplary knee-ankle-foot orthosis incorporating a variable stiffness module.
Figure 7:
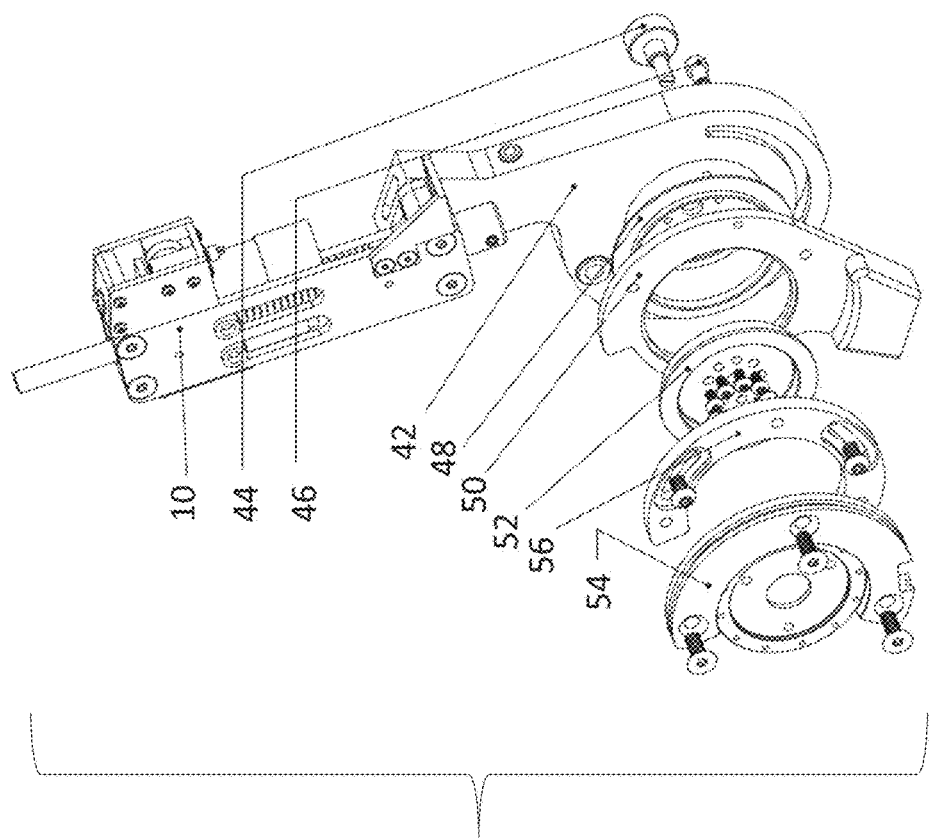
FIG. 7 is an exploded view of the knee-ankle-foot orthosis of FIG. 6.

As contemplated herein, the friction-based variable stiffness module 10 can be employed for various applications in the field of orthotics and prosthetics. For example, one such application includes a stance control knee orthosis that compliantly stabilizes the knee joint of the user. The orthosis demonstrates a high stiffness in the stance phase of the gait and a very low stiffness in the swing phase. Here, the friction-based variable module is assembled on a knee-ankle-foot orthosis (KAFO) 40 with a rope and pulley assortment as shown in FIG. 6. If the knee joint of the subject is flexed, the pulley turns and pulls the shaft of the stiffness module. The controller of the orthosis can detect if the foot is in contact with the ground or is off the ground. If the foot in on the ground, the stiffness module engages the high stiffness spring and vice versa. The components of an exemplary orthosis joint and pulley configuration are shown in FIG. 7, including a thigh chassis and circuitry enclosure or housing 42, potentiometer 44, rotation limit screw 46, bearing 48, shank chassis 50, pivot core 52, pulley 54 and pulley anchor 56. Functionally, the stiffness switching module engages the spring during the weight acceptance phase of the gait (or whenever support is required including standing), and allows nearly free motion in the rest of the gait. The stiffness switching module is mounted on thigh chassis 42 and, through a tendon, harnesses pulley 54 that is attached to shank chassis 50. As such, pulley 54 rotates when the knee flexes/extends, which then couples to the shaft of the stiffness switching module. Therefore, the linear stiffness exhibited at the shaft of the stiffness switching module is transformed to a torsional stiffness around the knee joint. A controller differentiates the knee joint angle obtained from potentiometer 44 incorporated in the orthosis lateral joint, and senses heel and toe contact with ground from an instrumented shoe insole (not shown).

Accordingly, the present invention may be characterized as a compliant stance control orthosis (CSCO) that is composed of a compliant stance control module (CSCM) integrated into a regular KAFO that lacks a lateral knee joint, as shown in FIG. 7. The CSCM includes a uniaxial joint setup, which functions as the lateral joint of the CSCO, and a CCM that exhibits two levels of stiffness through engagement/disengagement of a support spring. The lateral joint of the CSCO is primarily composed of the thigh chassis and shank chassis as well as the pulley and additional structural components. The CCM is assembled on the thigh and the pulley on the shank chassis. The CCM harnesses the shank chassis through a tendon attached to and wrapped around the pulley. The pulley rotates along with the knee joint, which, in turn, pulls the shaft of the CCM and compresses the return spring (and support spring, provided it is engaged). This transforms the linear stiffness of the CCM that is observed at the shaft to a torsional stiffness around the knee joint.

Figure 8:
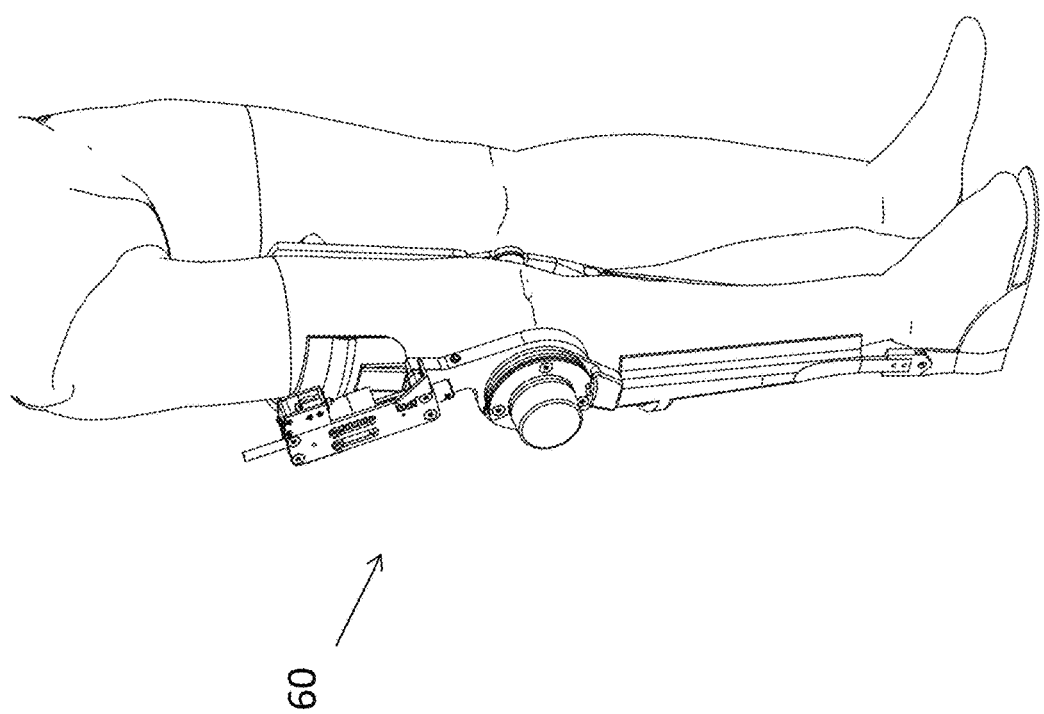
FIG. 8 is a schematic of an exemplary knee-ankle-foot orthosis incorporating a variable stiffness module further including a brushless DC motor and harmonic drive gear to accommodate swing-phase assistance.
Figure 9:
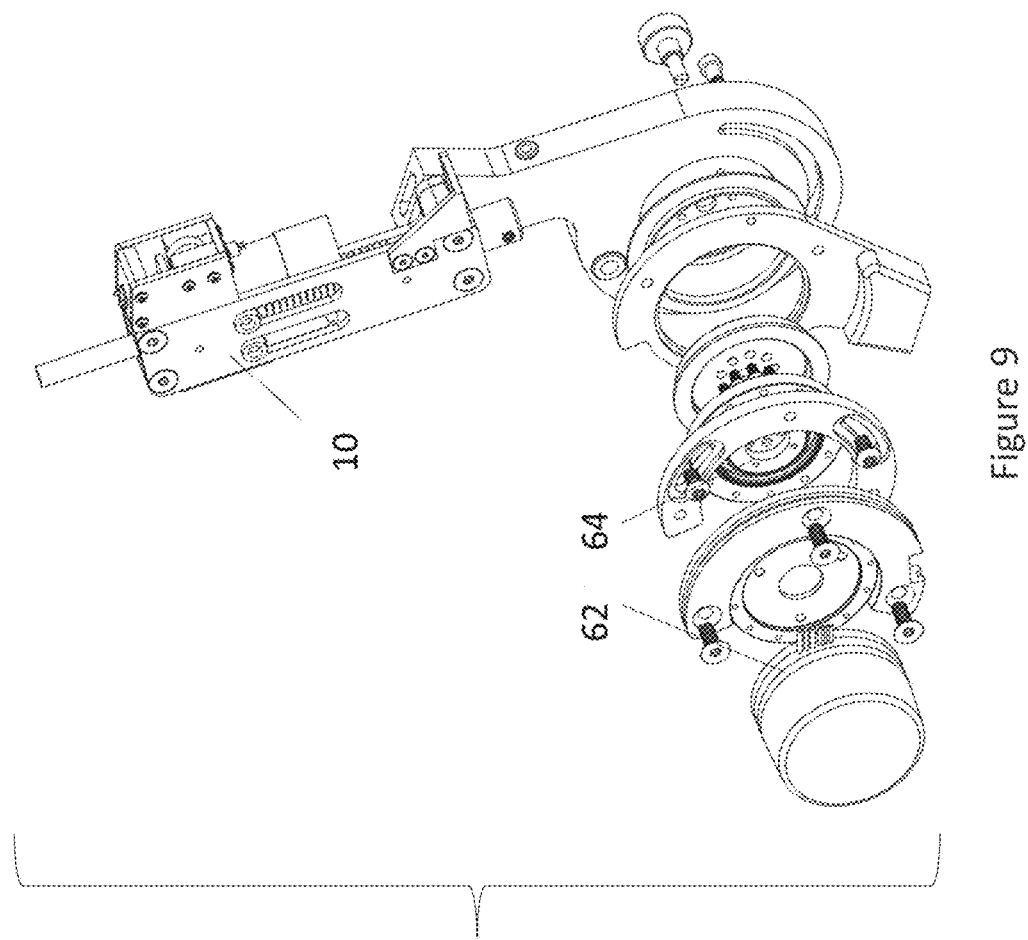
FIG. 9 is an exploded view of the exemplary knee-ankle-foot orthosis of FIG. 8.

In a further embodiment, the friction-based variable stiffness module can be assembled on a KAFO 60 as shown in FIG. 8 (similar to KAFO 40), and further including a brushless DC motor 62 and harmonic drive gear 64 to accommodate swing-phase assistance as shown in FIG. 9. For example, the swing-phase scheme can exploit a knee angle trajectory tracking algorithm, foot clearance with respect to the ground, knee torque trajectory tracking, and other possible algorithms [Kawamoto 2005, Chu 2005]. The brushless DC motor 62 can be replaced with any other actuator capable of providing the torque required to flex the knee in the swing phase. The harmonic drive 64 can be replaced with any other potential gearing system such as planetary gear, regular multi-stage gear and etc.

Figure 10:
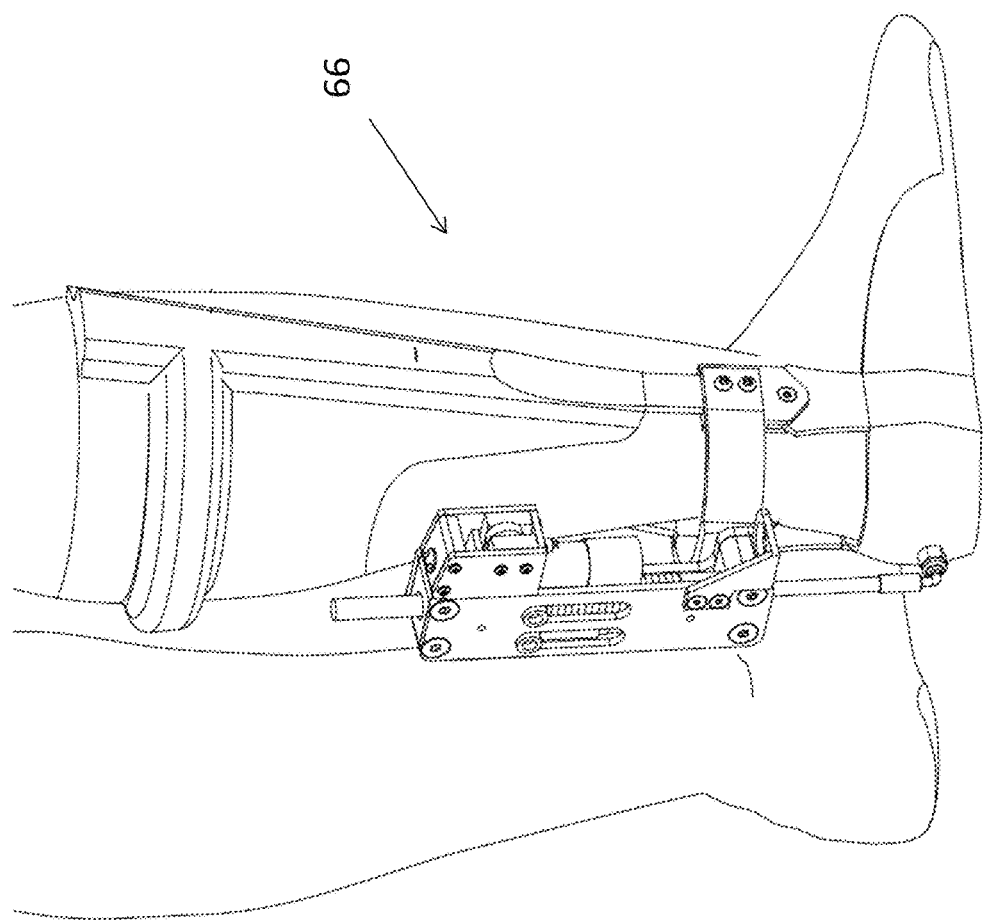
FIG. 10 is a schematic of an exemplary orthosis for a lower extremity joint incorporating a variable stiffness module.

In yet another embodiment, the friction-based variable stiffness module can be employed to orthoses and prostheses for other lower extremity joints including the ankle and hip. For example, an ankle orthosis design that employs the variable-stiffness module assembled on an ankle-foot orthosis (AFO) 66 that assists with walking is shown in FIG. 10. The variable-stiffness module 10 is mounted on the shank limb of AFO 66 and connected to the foot limb of the AFO 66 through a wire rope, metal rod or etc.

Control Algorithm

Figure 11:
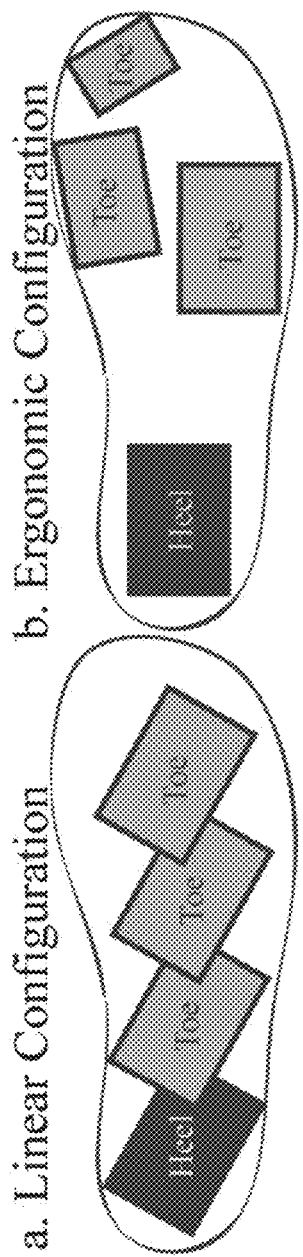
FIG. 11 is a schematic of the configuration of heel and toe sensors in the instrumented shoe insoles, a: Linear Configuration of force sensitive resistors (from OttoBock), and b: Ergonomic Configuration of integrated conductive polymers (from B & L Engineering). Both insoles resulted in relatively similar performance for level ground and treadmill walking.
Figure 12:
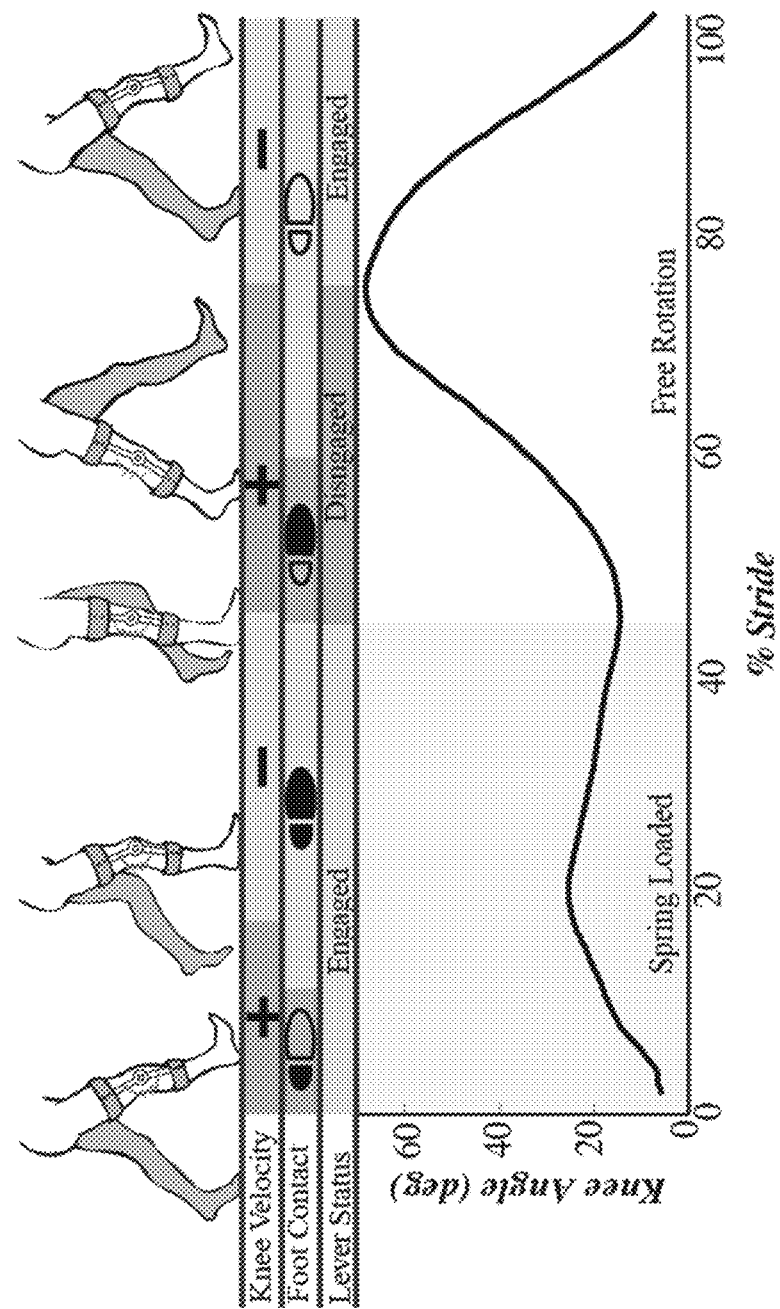
FIG. 12 is a schematic of the function of the CSCO. Top: The device engages a spring in the weight acceptance phase of the gait (and potentially the terminal stance depending on the needs of the user), Middle: The statuses of the knee motion, heel and toe contact with the ground, and engagement of the friction lever, Bottom: The knee angle profile for a healthy subject walking with the gait speed of 1.25 m·s-1.
Figure 13:
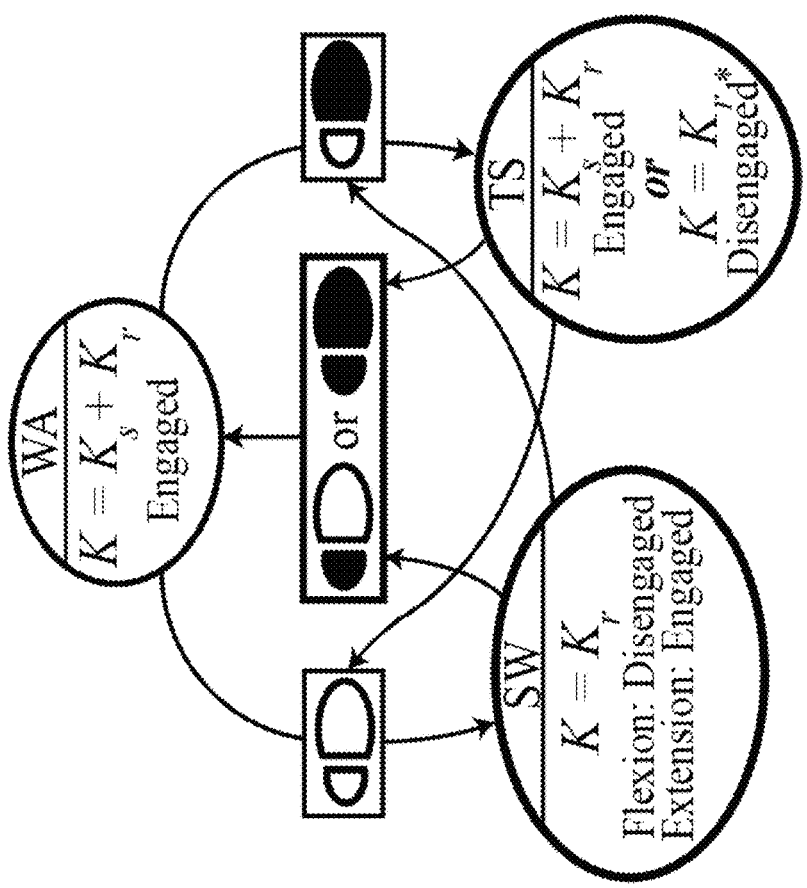
FIG. 13 is a schematic of the finite state machine used to control the stiffness of the compliance stance control module for level ground walking. The finite state machine includes three states: WA: Weight Acceptance, TS: Terminal Stance, and SW: Swing Phase. The transition between the state occurs when the status of foot contact with the ground changes. Each circle shows the stiffness of the compliance control module and status of the friction lever engagement.

The controller employs a finite state machine to engage and disengage the support spring. The controller identifies the gait phase by means of an instrumented shoe insole. In development of the present invention, two types of foot sensors were evaluated: a foot sensor with linear placement of force sensitive resistors (OttoBock) as shown in FIG. 11a, and a foot sensor with ergonomic placement of integrated conductive polymers (B & L Engineering) as shown in FIG. 11b. The function of the CSCO is schematically depicted in FIG. 12—top. FIG. 12—middle approximately outlines the knee angular velocity, foot contact with the ground, and the status of the friction lever. FIG. 12—bottom shows the knee angle profile for a subject walking at 1.25 m·s-1 on level ground and the period during which the support spring is intended to be engaged and loaded. FIG. 13 describes the finite state machine that is implemented to control the CCM for walking on level ground. The states include:

a. Weight Acceptance (WA):
Either the heel sensor is on or both heel and toe sensors are on. The controller engages the support spring.

b. Terminal Stance (TS):
Any of the toe sensors are on and the heel is off. If the user can maintain stability during this phase, the CCM can disengage the support spring; otherwise, the support spring can remain engaged. The ability of the user to maintain stability can be evaluated by an orthotist/physician and programmed into the device.

c. Swing (SW):
The toe and heel sensors are off. The controller monitors the knee velocity direction during the swing phase to identify the flexion and extension period of knee excursion in the swing phase. The controller disengages the support spring during the flexion period of the swing phase and engages it during the extension period, as a precautionary measure against the mechanism's latching latency. Although the friction lever is engaged during the extension period of swing phase, the support spring is loaded because the engagement mechanism only initiates a latch in the flexion direction.

Preferably, a microcontroller MPC5534 from Freescale Semiconductor Co. (MPC5534EVBE) is used to implement the finite state machine for two CSCOs (left and right orthoses). The controller measures the knee angle using the rotary potentiometer (Model 357, Vishay Co.) that is integrated inside the orthosis pulley, and the knee velocity is obtained by differentiating the potentiometer signal. The controller identifies the status of the friction lever using the signals received from the push-buttons incorporated in the CCM. More specifically, the signal from the spring-loaded push-button defines if the friction lever is disengaged, while the signal from the retreat push-button defines if the friction lever is engaged. A serial-to-Bluetooth adapter (Wireless RS232, Willies Computer Software Co.) establishes wireless transfer of data to a host LabView module implemented on a computer for data collection. A dual H-Bridge from Solarobotics Co. was used to drive a Faulhaber 2024 DC Motor that was used in the design of the CCM as described in the Examples herein. A battery pack with capacity of 2500 mAh powers the controller, orthosis and the wireless connection systems.

Design Analyses and Characterization

Figure 14:
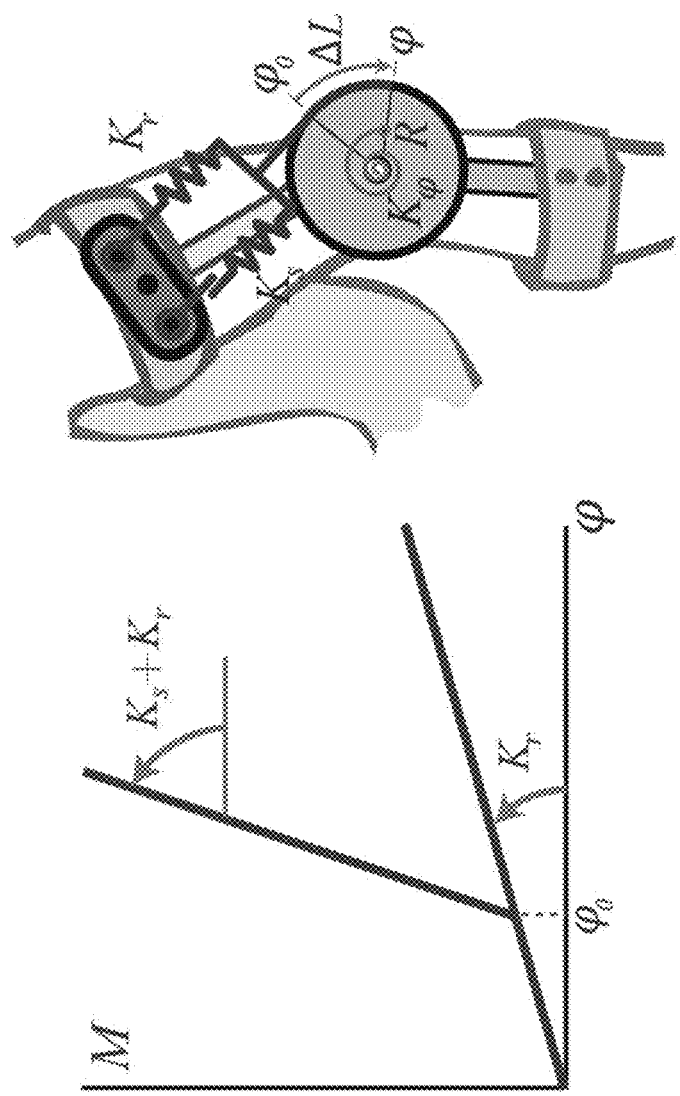
FIG. 14 includes a schematic configuration of the return and support springs. The output stiffness of the compliance control module is the summation of the spring constants of both springs if the support spring is engaged, and only the spring constant of the return spring otherwise. The springs apply a force on the pulley with radius R. The effect of the linear return stiffness $K_r$ and support stiffness $K_s$ is experienced as an imaginary torsional spring around the center of the pulley with torsional stiffness $K\phi$.

The CSCO tendon is wrapped around and anchored to the pulley that is mounted on the shank chassis. When the knee flexes, the return spring (and support spring if engaged) will compress and apply a moment on the pulley, as schematically shown in FIG. 14—top. This moment can be calculated as:

$$M = K_L \cdot \Delta L \cdot R \quad (1)$$

where, R is the radius of the pulley and $K_L$ is the linear stiffness of the CCM observed at the shaft. Also, a knee flexion of $\Delta\phi$ results in a shaft movement of $\Delta L$. Thus, the stiffness of an imaginary linear torsional spring $K\phi$ that can replace the transformed stiffness CCM around the knee would be:

$$K\phi = K_L \cdot \Delta L \cdot R/\Delta\phi \quad (2)$$

And since $\Delta L = R\Delta\phi$, it is concluded that:

$$K\phi = K_L \cdot R^2 \quad (3)$$

$K_L$ is the stiffness of the return spring when the friction lever is disengaged and the summation of the stiffness of both springs when the support spring is engaged:

$$K_L = \begin{cases} K_r + K_s & \text{engaged} \\ K_r & \text{disengaged} \end{cases} \quad (4)$$

Combining equation (3) and (4) gives:

$$K_\psi = \begin{cases} (K_r + K_s) \cdot R^2 & \text{engaged} \\ K_r \cdot R^2 & \text{disengaged} \end{cases} \quad (5)$$

This suggests the following equation for the assistive moment observed at the knee joint:

$$M = \begin{cases} K_r \cdot R^2 \cdot \varphi + K_s \cdot R^2 \cdot (\varphi - \varphi_0) & \text{engaged} \\ K_r \cdot R^2 \cdot \varphi & \text{disengaged} \end{cases} \quad (6)$$

Here, $\phi_0$ is the angle at which the support spring is engaged. FIG. 14—bottom shows the theoretical moment-angle performance of the CSCO.

Figure 15:
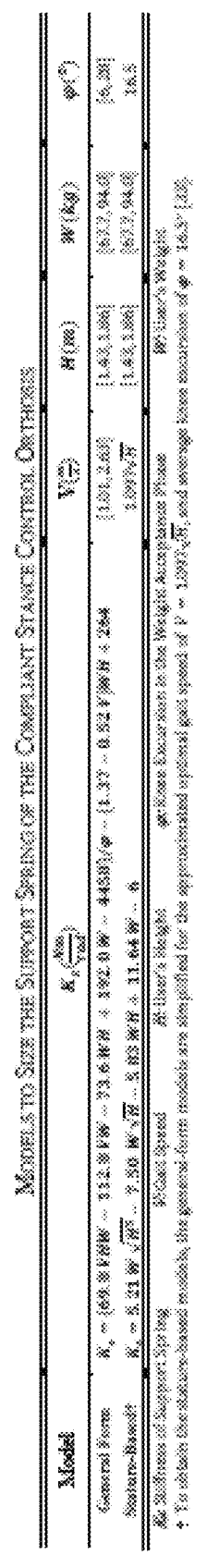

Selection of a preferred support spring can help the device implement a natural amount of compliance and minimize the compensatory movements of the body. As explained herein, the knee's function can be replaced by a torsional spring with a stiffness equal to the knee quasi-stiffness in the stance phase. A subject's knee and ankle quasi-stiffnesses significantly depend on body size and gait conditions. Current prosthetic design approaches usually employ the joint quasi-stiffness of healthy subjects with average weight and height, which requires substantial effort and time to conduct a gait lab study for each target user size, and additional tuning for the specific patient. Alternatively, a series of statistical models that can estimate the quasi-stiffnesses of the knee and ankle joints in the stance phase of the gait can be used. FIG. 15 lists the most general and simplified forms of the statistical models that estimate the knee quasi-stiffness in the weight acceptance phase. The most general model tends to provide a closer estimation of the knee quasi-stiffness for a wide range of gait speed (1.01 ms-1 to 2.63 ms-1), weight (67.7 kg to 94.0 kg), height (1.43 m to 1.86 m), and knee excursion (6 deg to 28 deg), whereas the stature-based model estimates the knee quasi-stiffness only at the preferred gait speed and trades accuracy for simplicity by approximating the knee excursion and gait speed. These statistical models may be exploited to size the support spring of the device for users with complete impairment. For other users, the support spring stiffness can be a function of the level of impairment of the knee joint.

Figure 16:
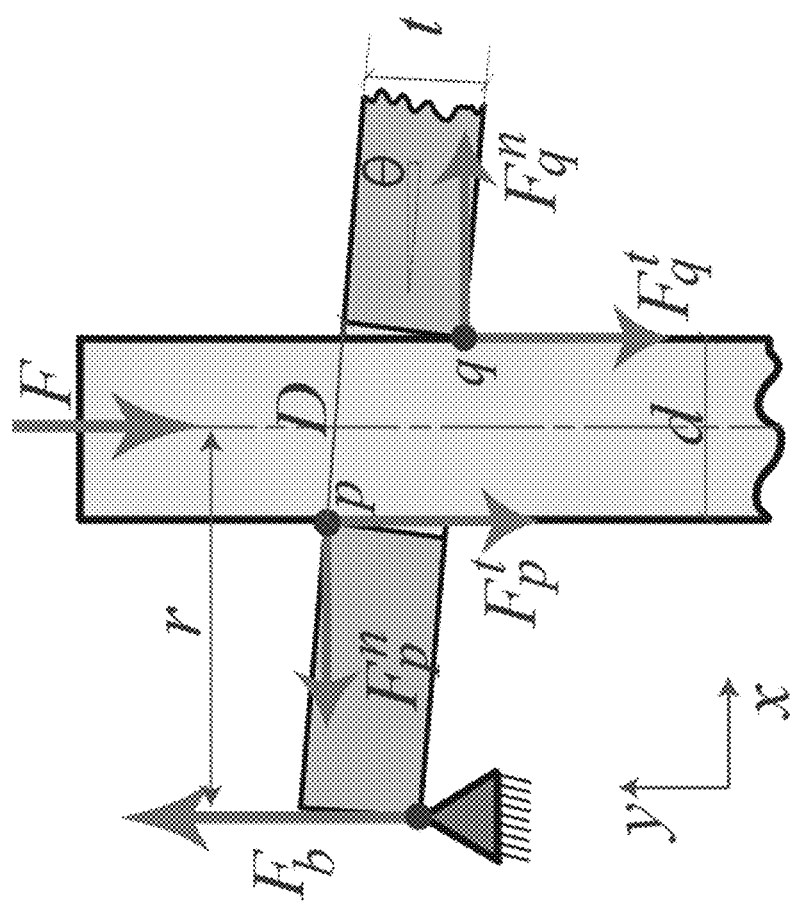
FIG. 16 is a free body diagram of the friction lever under the interaction with the shaft and bearing block. The interaction force from the bearing block $F_b$ generates normal forces between the friction lever and the shaft $F_p''$ and $F_q''$; inducing tangential friction forces $F_p^t$ and $F_q^t$. If the moment arm r is long enough, latching occurs and the shaft, friction lever, and bearing block lock together.

FIG. 16 shows the free body diagram of the friction lever. It is assumed that an initial moment around the point of contact between the lever and bearing block b (e.g. caused by the weight of the lever and the spring-loaded push-button) brings the friction lever in contact with the shaft at two points p and q. The interaction force between the lever and bearing block Fb, which is identical to the shaft force F, induces friction forces between the lever and shaft, Fp and Fq. Therefore, the normal friction forces are proportionate to the moment-arm around the center of the shaft r. A relationship is derived between r, and the friction lever thickness t and diameter D under which the friction forces cause a latching grip between the shaft and friction lever.

The friction lever is stationary in the direction perpendicular to the shaft, therefore:

$$\Sigma F_x = 0 \quad (7)$$

where $F_x$ denotes any force applied on the friction lever along the x-axis. The normal contact forces at p and q (i.e. $F_p^n$ and $F_q^n$) cause the tangential friction forces $F_p^t$ and $F_q^t$ on the friction lever. Expanding equation (7) concludes:

$$F_p^n = F_q^n \quad (8)$$

which in turn implies that the friction forces are equal:

$$F_p^t = F_q^t \quad (9)$$

Since the lever is stationary around b, the summation of moments applied on the lever should be zero around this point:

$$\Sigma M_b = 0 \quad (10)$$

where, $M_b$ stands for any moment applied on the friction lever around an axis passing through b and perpendicular to the plane of movement. Expanding equation (10) and including equation (9) gives:

$$F_p^n(D \cdot \sin\theta + t \cdot \cos\theta) - F_p^t(2r) = 0 \quad (11)$$

where D is the diameter of the hole of the friction lever, t is the thickness of the friction lever, and $\theta$ is the tilt angle of the friction lever with respect to the x-axis. In order for the friction lever to engage with the shaft, the friction forces should remain lower than the maximum friction force:

$$F_p^t \leq F_p^n \cdot \mu \quad (12)$$

where $\mu$ is the coefficient of friction between the shaft and lever. Applying equation (11) in (12) concludes:

$$r \geq \frac{D \cdot \sin\theta + t \cdot \cos\theta}{2\mu} \quad (13)$$

For small tilt angles (i.e. $\theta \sim 0$), equation (13) can be simplified to:

$$r \geq \frac{t}{2\mu} \quad (14)$$

Moreover, the maximum normal stress ($\sigma_{max}$) imposed by the interaction forces between the friction lever and shaft should not exceed the material's yield strength ($\sigma_Y$):

$$|\sigma_{max}| \leq \frac{\sigma_Y}{s} \quad (15)$$

Here, S is a safety factor. The maximum normal stress occurs at the outer surface of the friction lever between points b and p:

$$\sigma_{max} = \frac{3Fr}{wt^2} + \frac{F}{wt}\sqrt{9\left(\frac{r}{t}\right)^2 + 1} \quad (16)$$

where, w is the width of the friction lever. Combining equations (15) and (16) concludes:

$$\frac{3r}{t} + \sqrt{\left(\frac{3r}{t}\right)^2 + 1} \leq \frac{3wtR\sigma_Y}{M_{Knee}S} \quad (17)$$

where $M_{Knee}$ is the maximum knee moment that the device experiences. When a steel shaft is employed and friction lever with case hardness of Rockwell C60-C64, that theoretically exhibits a lubricated static coefficient of friction of 0.15 and yield strength of ~670 MPa. The shaft diameter is 9.525 mm (⅜ in) and the lever thickness 3.175 mm (⅛ in). Considering a safety factor of 1.5 and $M_{Knee}$ of 110 N·m, the bearing block contact point should be 20 mm away from the center of the shaft.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Design and Compliance Testing of a Stance Control Orthosis

Figure 17:
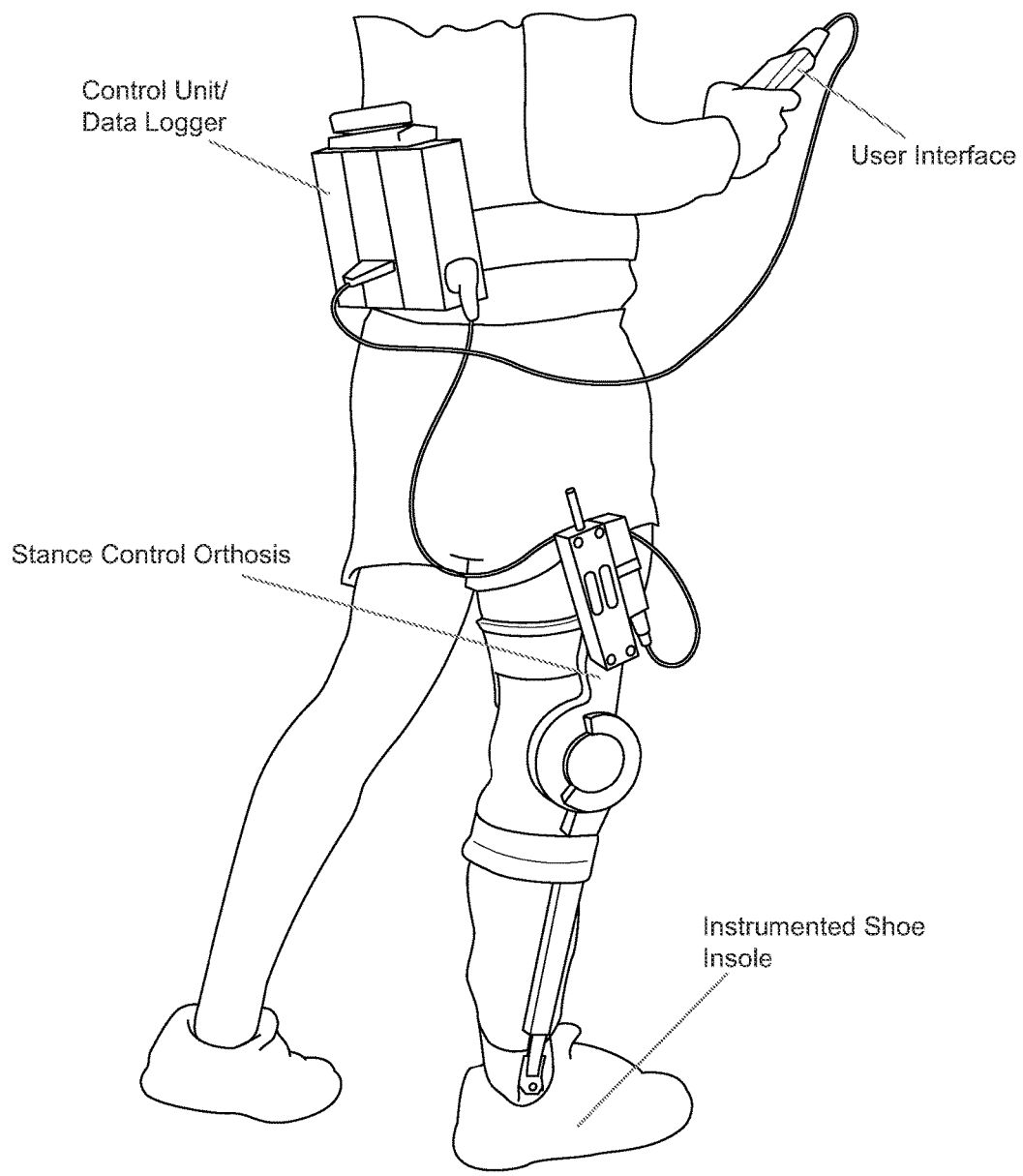
FIG. 17 is a photograph of a constructed quasi-passive complaint stance control Knee-Ankle-Foot-Orthosis of Example 1.

As shown in FIG. 17, a quasi-passive complaint stance control orthosis (SCO) was constructed that supports the knee in the stance phase of the gait by implementing a spring in parallel with this joint (as an improvement to the current devices that rigidly lock the knee in stance), and allows for free motion in the rest of the gait. It is demonstrated herein how the SCO exhibits multiple levels of stiffness at different phases of the gait through engagement and disengagement of a linear spring in parallel with the knee. The control algorithm decides whether to engage the spring depending on the gait phase, and how the spring stiffness and assistance duration can be adjusted for users with different forms and levels of impairment.

Moment-Angle Performance of Healthy Knee

Figure 18:
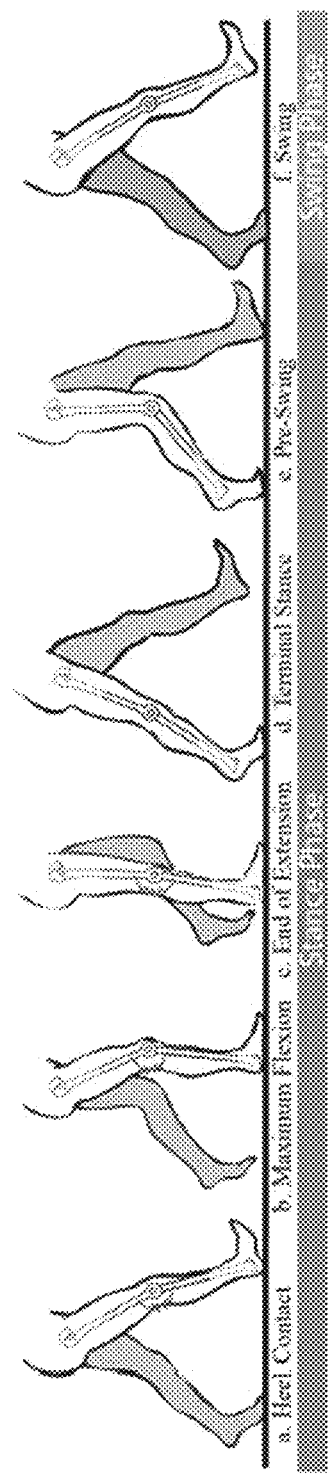
FIG. 18 is a schematic posture of the lower limbs during a gait cycle that shows when the variable stiffness module should switch to high stiffness during the stride cycle.
Figure 19:
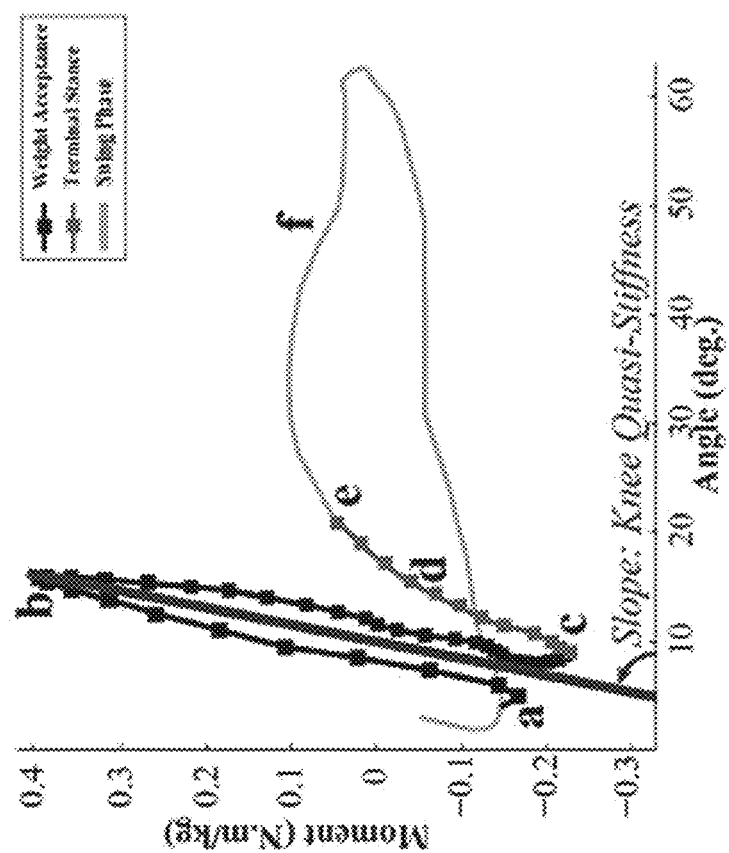
FIG. 19 is an average moment-angle graph for the knee of a set of subjects walking at slow cadence of 85 step/min. The knee behaves linearly in the weight acceptance phase of stance implying that an impaired knee can be stabilized by an external spring.

FIG. 18 shows the schematic posture of the lower extremity limbs during a gait cycle and FIG. 19 shows the moment angle graph of the knee in walking on level ground for a healthy individual with the corresponding schematic configurations labeled. The gait cycle was divided into a stance and a swing phase. The stance phase was further divided into a weight acceptance phase (first ~40%, as depicted in FIGS. 18 and 19 points a to c) and a stance termination phase (~40-63%, as shown in FIGS. 18 and 19 points c to e) (Winter, 1983, J Mot Behav 15(4):302-30; Rose and Gamble, "Human walking," 3rd ed., Philadelphia: Lippincott Williams & Wilkins, 2006; Shamaei and Dollar, 2011, IEEE Int Conf Rehabil Robot 2011:5975478; J. Perry, "Gait analysis: normal and pathological function," Thorofare, N.J.: SLACK, 1992; D. Winter, "The biomechanics and motor control of human gait: normal, elderly and pathological," 2nd ed., Waterloo, Ont.: University of Waterloo Press, 1991). As shown in FIG. 19, the knee exhibits a large moment and considerable flexion in the weight acceptance phase that follows a linear moment-angle pattern (Shamaei and Dollar, 2011, IEEE Int Conf Rehabil Robot 2011: 5975478). Considering the large moment that the knee is required to generate during the weight acceptance phase, it is highly prone to collapse at this phase without proper function of the musculature system or external assistance. The knee behaves close to a very stiff torsional spring (average ~3 Nm/rad·kg) that is dramatically loaded (0.5 N/m·kg) at the preferred gait speed (Shamaei and Dollar, 2011, IEEE Int Conf Rehabil Robot 2011:5975478). The knee displays substantially smaller moments in the rest of the gait cycle that could imply a less eminent need for external assistance.

Design Objectives

The biological moment-angle behavior of an unaffected knee can imply that in order for a SCO to mimic the behavior of the knee in the weight acceptance phase, it should function close to a linear torsional spring. More specifically, the SCO should engage a spring (sized based on the subject's stature and speed) at the onset and disengage it at the end of the weight acceptance phase. The variability of kinematic parameters as well as the quasi-stiffness and work of the ankle and knee joints has previously been investigated (Shamaei and Dollar, 2011, IEEE Int Conf Rehabil Robot 2011:5975478; Shamaei et al., 2011, Conf Proc IEEE Eng Med Biol Soc 2011:8135-40). It was found that the knee excursion ranges from 2° to 30° in the weight acceptance phase of the gait. This indicates that the SCO should have a very high angular engagement resolution to be able to capture the natural knee flexion in stance. The angle of equilibrium of the torsional spring equivalent to the knee can attain values of up to 32°, depending on the gait speed and carried weight, implying that the angle of engagement should also be adjustable. The weight acceptance phase spans ~40% of the gait that corresponds to a period of ~450 ms, implying that the engagement and disengagement of the assistive device spring should ideally be instantaneous to be responsive in the weight acceptance period. Thus, the knee quasi-stiffness modulates based on the gait speed and carrying weight. The SCO design should be capable of displaying a stiffness up to ~750 nm/rad and a maximum moment of ~105 nm/rad (selectable by changing out the spring to size for the specific individual) to be able to function for a wide range of adults (Shamaei and Dollar, 2011, IEEE Int Conf Rehabil Robot 2011:5975478). Torsional springs provide substantially smaller range of stiffness as long as they remain within a reasonable size limit suitable for the desired application. Alternatively, linear springs tangential with a circular pulley can be used to exhibit the range of torsional stiffness required to support the knee. The SCO should also be as light as possible. A target weight of 3 kg similar to that of other commercial SCOs such as the SensorWalk from OttoBock was chosen. Additionally, the device should demonstrate minimal electric power consumption and noise generation, as well as reasonable cosmetic appearance. Table I summarizes the target requirements for the design of the SCO.

TABLE I

Target and Realized Values for the Design Parameters

| Design Parameter | Target | Realized |
| --- | --- | --- |
| Joint Excursion Under Load | 25° | 40° |
| Angular Resolution | 1° | <1° |
| Engagement Delay | 0 ms | 40 ms |
| Maximum Moment | 105 N · m | >105 N · m |
| Stiffness | <750 nm/rad | ~∞ |
| Angle of Engagement | 6-32° | 0-60° |
| Weight | 3 kg | 3 kg |

Description of the Stance Control Orthosis

FIG. 17 shows the SCO worn on a healthy subject. The SCO is composed of an orthotic device that is cuffed on the leg, and a control and recording module that is belted behind the waist of the subject. Note that this control module is much larger in order to allow for a range of telemetry and data collection purposes. As contemplated herein, the control module can be reduced to the size of a stack of business cards, for example.

Figure 20:
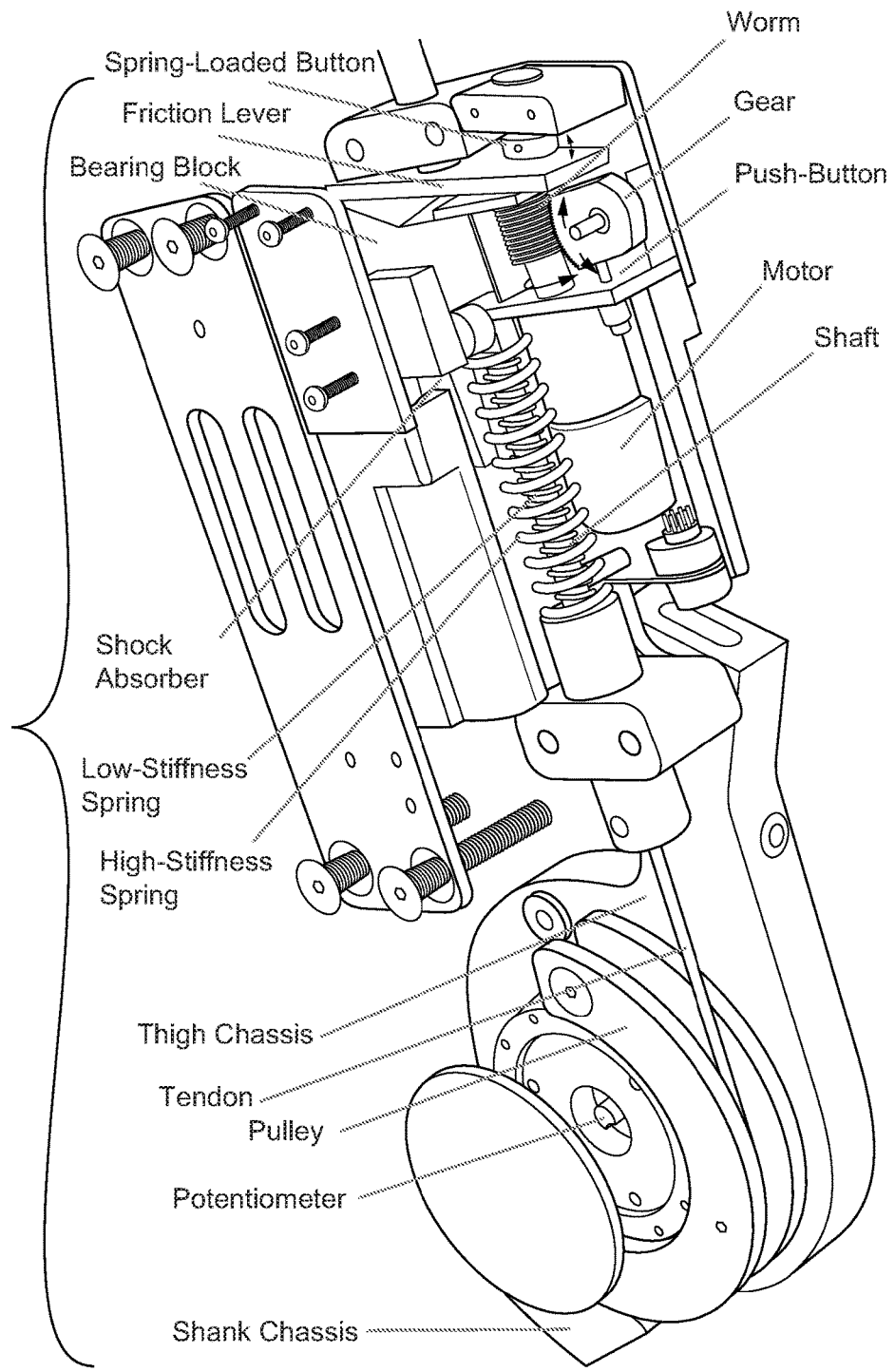
FIG. 20 is an exploded view of the orthotic device constructed in Example 1, including the stiffness switching module that harnesses the pulley of the lateral joint of the stance control orthosis.

The orthotic device includes a stiffness switching module and a lateral joint designed for the SCO, as illustrated in FIG. 20. Also shown in FIG. 20 are the components of the engagement mechanism and the lateral joint. The stiffness switching module engages a spring during the weight acceptance phase of the gait (or whenever support is required including standing), and allows nearly free motion in the rest of the gait. The stiffness switching module is mounted on the orthosis thigh and, through a tendon, harnesses a pulley that is attached to the orthosis shank. As such, the pulley rotates when the knee flexes/extends, which then couples to the shaft of the stiffness switching module. Therefore, the linear stiffness exhibited at the shaft of the stiffness switching module is transformed to a torsional stiffness around the knee joint.

The controller receives the knee angle, the status of the heel and toe contact with the ground (through the FSR insoles), and the status of the device stiffness, and determines the engagement. It further wirelessly transfers data to a host computer for experimental purposes.

Stiffness Switching Module

The stiffness switching module employs a friction-based latching mechanism and primarily comprises a hardened shaft, friction lever, bearing block, shock absorber, and an engagement mechanism that includes a worm-gear set, a DC motor, two push-buttons for feedback on the position of the lever, and structural components, as shown in FIG. 20. In this example, the latching friction lever is being manipulated with a reliable mechanism that can automatically engage/disengage it with a shaft. As shown in FIG. 20, the motor spins a worm-gear that in turn moves a custom-made gear away/toward the lever. The gear can accordingly engage or disengage the friction lever with the hardened shaft.

Figure 21:
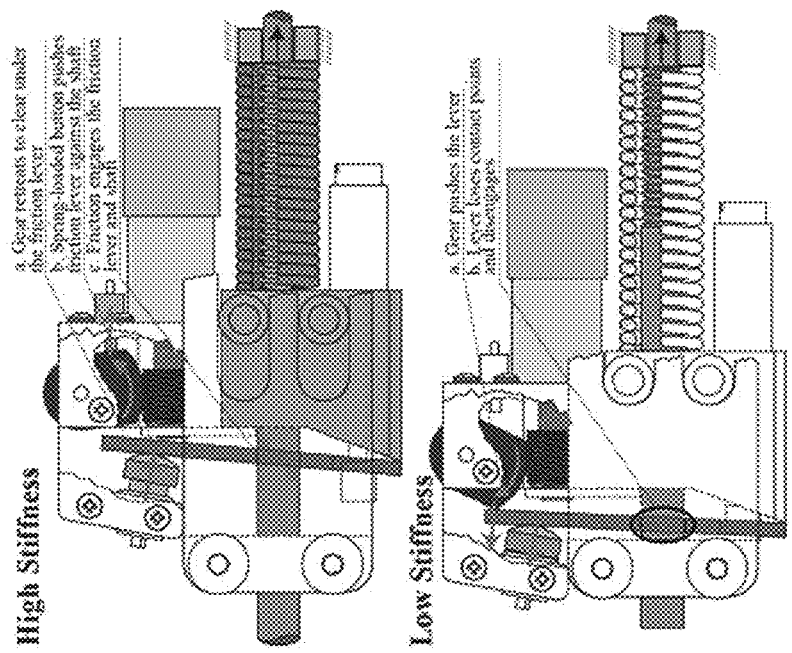
FIG. 21 is a schematic of high and low stiffness configurations. (Top) Engagement of high-stiffness spring: When the friction lever is engaged, flexion of the knee compresses both the low stiffness and high stiffness springs of the variable-stiffness module; (Bottom) disengagement of high-stiffness spring: When the friction lever is disengaged, flexion of the knee only compresses the low stiffness spring (which is mainly incorporated to return the shaft in the extension period). Only those parts of the variable-stiffness module that are involved in each mode are colored.

FIG. 21 shows the stiffness module under two loading conditions: high-stiffness and low-stiffness. To engage the high-stiffness spring, the motor spins counterclockwise that moves the gear away from the friction lever as shown in FIG. 21 (top) to clear behind the friction lever and press the pushbutton located behind it. When the gear is away from the lever, the spring loaded push-button pushes the friction lever that initiates the engagement of the friction lever to the shaft. Upon a load to the shaft, the engaged friction lever transfers the force of the loading shaft to the bearing block. Therefore, the shaft force tends to move the bearing block that, in turn, compresses the high-stiffness spring. The shaft force always compresses the low-stiffness spring. Therefore, the module exhibits an output stiffness that is equal to the summation of the stiffness of both springs.

In order to disengage the high-stiffness spring, the motor spins clockwise that moves the gear toward the lever as shown in FIG. 21 (bottom). The gear pushes the friction lever away from the motor until the spring loaded push-button is pressed. In this configuration, the shaft can slide inside the bearing block and the friction lever. Therefore, any force on the shaft only compresses the low-stiffness spring. As such, the module only displays the low stiffness of the internal spring at the output. The shock absorber is incorporated to dissipate any remaining potential energy in the high-stiffness spring, provided it is still compressed when it is disengaged.

To transform the linear stiffness of the spring to a rotational stiffness around the knee, it is assumed that a knee flexion of $\Delta\theta$ causes a compression of $\Delta L$ in the spring. The equivalent torsional stiffness around the knee would be calculated as:

$$K_\theta \cdot \Delta\theta = K_L \cdot \Delta L \cdot r \quad (18)$$

where $K_\theta$ is the equivalent torsional stiffness exhibited at the knee joint, $K_L$ is the linear stiffness of the stiffness switching module, and r is the radius of the pulley.

Considering $\Delta L = r\Delta\theta$, we obtain:

$$K_\theta = K_L \cdot r^2 \quad (19)$$

Therefore, to satisfy the range of torsional stiffnesses, the linear spring should have a stiffness of up to ~290 N/mm for a pulley radius of 51 mm (2 in.). Table I (above) lists the values for the design parameters measured on the device.

Control Unit and Data Logger

Figure 22:
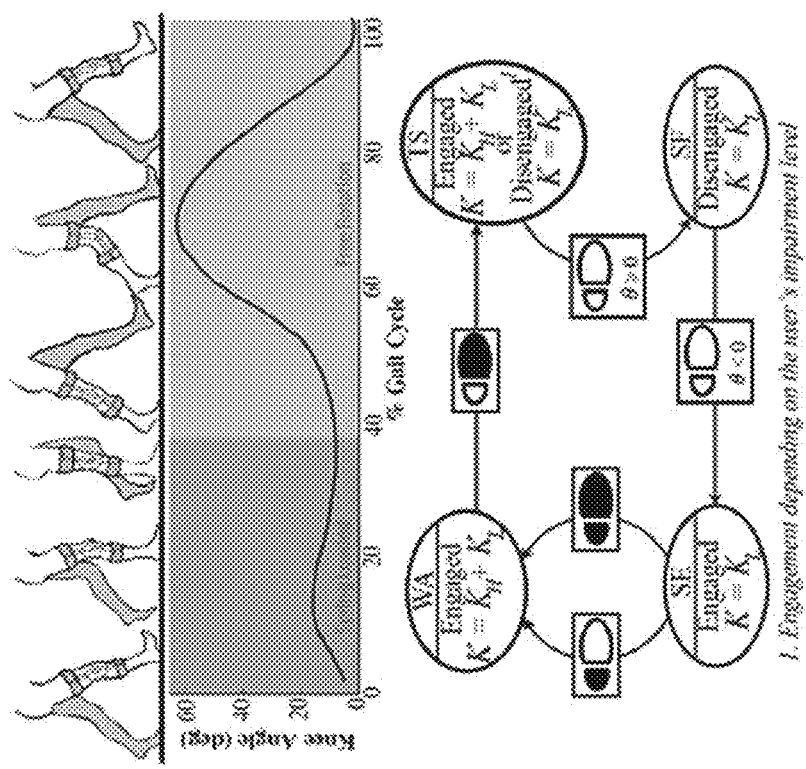
FIG. 22 (Top) is a schematic function of the stance control orthosis; (Middle) is a graph of the knee angle profile for a healthy subject walking at the slow cadence of 85 steps/min; (Bottom) is schematic of the state-machine employed for the control of the stance control orthosis in level ground walking WA: Weight Acceptance, TS: Terminal Stance; $K_H$: High-Stiffness Spring Constant; $K_L$: Low-Stiffness Spring Constant.

The controller engages the high-stiffness spring during the weight acceptance phase by monitoring the direction of the knee joint velocity and foot contact with the ground, as schematically shown in FIG. 22 (top) and detailed here. The controller differentiates the knee joint angle obtained from a rotary potentiometer incorporated in the orthosis lateral joint, and senses the heel and toe contact with ground from an instrumented shoe insole.

FIG. 22 (middle) shows the knee angle in a gait cycle (data from Winter, 1983, J Mot Behav 15(4):302-30) and the period of engagement, in addition to FIG. 22 (bottom) that shows the state machine implemented to control the level of stiffness of the SCO. The SCO switches to high stiffness when the knee is in extension period of the swing phase (pre-stance phase when the heel and toe sensors are off) as a precaution against the mechanism switching delay. Since the knee is in extension mode, the high-stiffness spring is not loaded because the engagement mechanism only latches in the flexion direction. When the heel contacts the ground, the lever remains engaged. At this point, the knee starts flexing and as a result the high-stiffness spring is loaded. The spring remains engaged when the foot is flat (i.e. both the heel and toe are in contact with the ground). The leg goes into the terminal stance phase when the toe is on the ground. The spring would disengage during the terminal stance for users who require external stabilization only during the weight acceptance phase. For users who require assistance during the entire stance phase (e.g. in case of complete impairment of the knee), the spring would remain engaged until the toe leaves the ground.

The data logger simultaneously records data obtained from the device and wirelessly transfers them to a host computer, provided data transfer is required. The data logger allows for recording and transfer of up to 24 analog and digital channels. The controller transfers the knee angle and velocity, foot sole force, orthotic assistive moment, engagement status, and gait phase. The controller is also equipped with a user-interface that allows for synchronization of the device with the gait lab system, changing the control algorithm, emergency stop, and additional options for experimental purposes.

Figure 23:
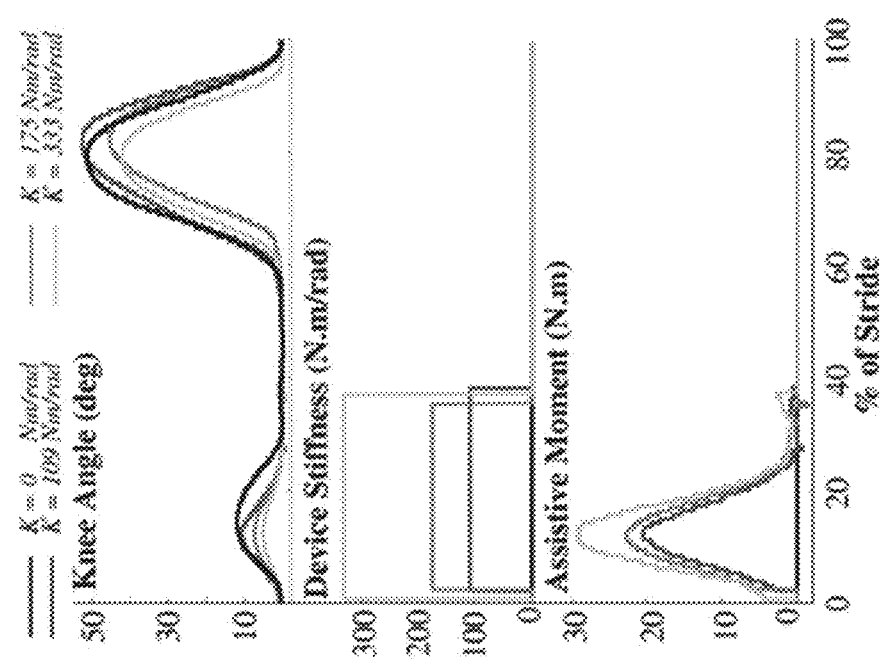
FIG. 23 is a graph depicting kinetic and kinematic data obtained from the stance control orthosis for a healthy subject with the height of 1.78 m and weight of 71 kg, walking at speed of 0.6 m/s on a treadmill. The orthosis employed three levels of stiffness including 109 nm/rad, 175 nm/rad, and 333 nm/rad as well as natural walking (0 nm/rad); (Top) Knee joint angle; (Middle) Device stiffness; and (Bottom) Device assistive moment.
Figure 24:
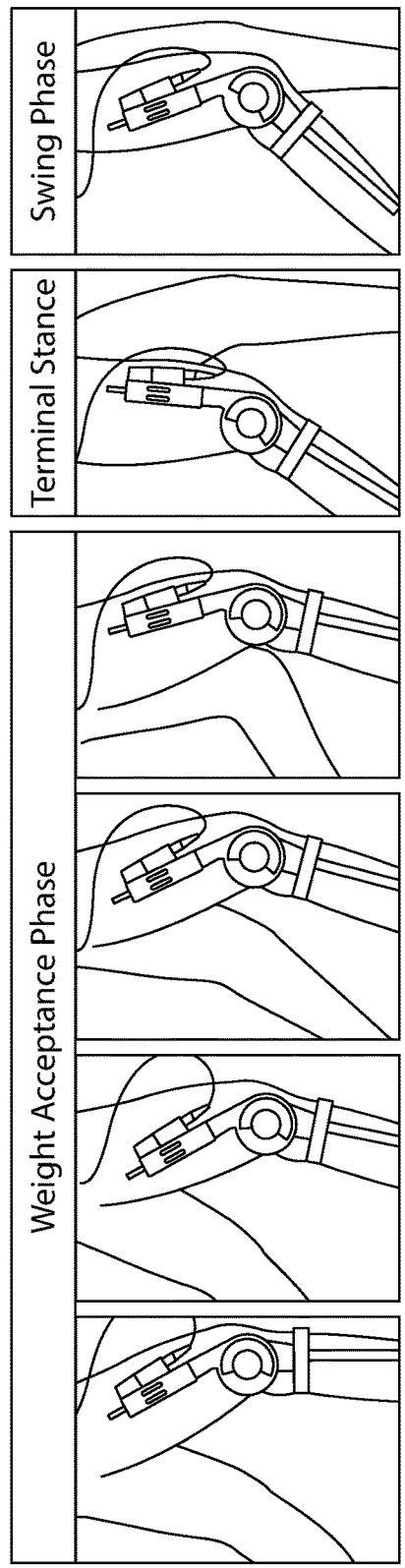
FIG. 24 is a series of photographs of a healthy subject wearing the stance control orthosis and walking on a treadmill. The orthosis stabilizes the knee by implementing a sized spring in parallel with it during the weight acceptance phase of the gait and allows for free (low-stiffness) rotation during the rest of the gait.

FIG. 23 shows the data obtained from the device for the treadmill gait of a healthy subject with height of 1.78 m and weight of 71 Kg, and gait speed of 0.6 m/s. The subject wore the device under four conditions: a. Three different high stiffness springs: 109, 175, and 333 Nm/rad, and b. Natural walking wearing the device and without the orthotic assistance. FIG. 23 (top) shows the knee angle, (middle) the device stiffness, and (bottom) the device assistive moment. Moreover, FIG. 24 shows the gait of a healthy subject wearing the SCO and walking on a treadmill. Here, the orthosis employs a spring with stiffness of 109 Nm/rad and provides assistance only during the weight acceptance phase of the gait.

Accordingly, Example 1 presents the mechanical design and control algorithm for a SCO that can stabilize an impaired knee by implementing a spring in parallel with this joint in the stance and allow for free rotation during the swing phase of the gait. Here, the implemented compliance in the SCO was biologically inspired from the moment-angle analyses of a healthy human knee. The constructed SCO demonstrates improved performance over existing SCOs that rigidly lock the knee during the stance phase and allow free rotation during the swing. The potential benefits include a reduction in the compensatory movements of the unaffected joints, restoring the shock absorption function of the knee flexion in the stance, higher gait speed, and longer walking distances/intervals.

The present invention can be used to restore the natural gait of users with gait impairment following injury, stroke, post-polio, multiple sclerosis, SCI, Patellofemoral Pain Syndrome, or any other musculoskeletal dysfunction that causes quadriceps weakness. The present invention can employ different levels of torsional stiffness and period of assistance depending on the level of functionality or impairment of the knee.

The constructed SCO satisfied nearly all the design criteria that were established based on the biomechanical behavior of healthy knee joint, as outlined in Table I. Those criteria included high angular engagement resolution, instantaneous engagement, high angular stiffness, wide range of motion, variable angle of engagement, low noise generation, light weight, and low power consumption. The present invention may employ high-speed steel for the material of the friction lever, and in other embodiments, steels with higher hardness may be employed to increase the endurance of the device.

It should be appreciated that both the orthosis and controller of Example 1 were overdesigned and can be made smaller and lighter. For example, the control unit can be made significantly smaller and more efficient by eliminating the data logging and transfer functionality such that the controller and battery pack can be implemented and embedded inside the lateral joint of the SCO, saving space and reducing the power consumption of the device.

Example 2: Mechanical and Functional Evaluation

Three additional tests were conducted to evaluate/measure the reliability, latency and endurance of a CSCO, and also the kinematic performance of three healthy volunteers using the CSCO, including a comparison to a commercial SCKAFO (Sensor Walk by Otto Bock).

Preclinical Static Loading

Figure 25:
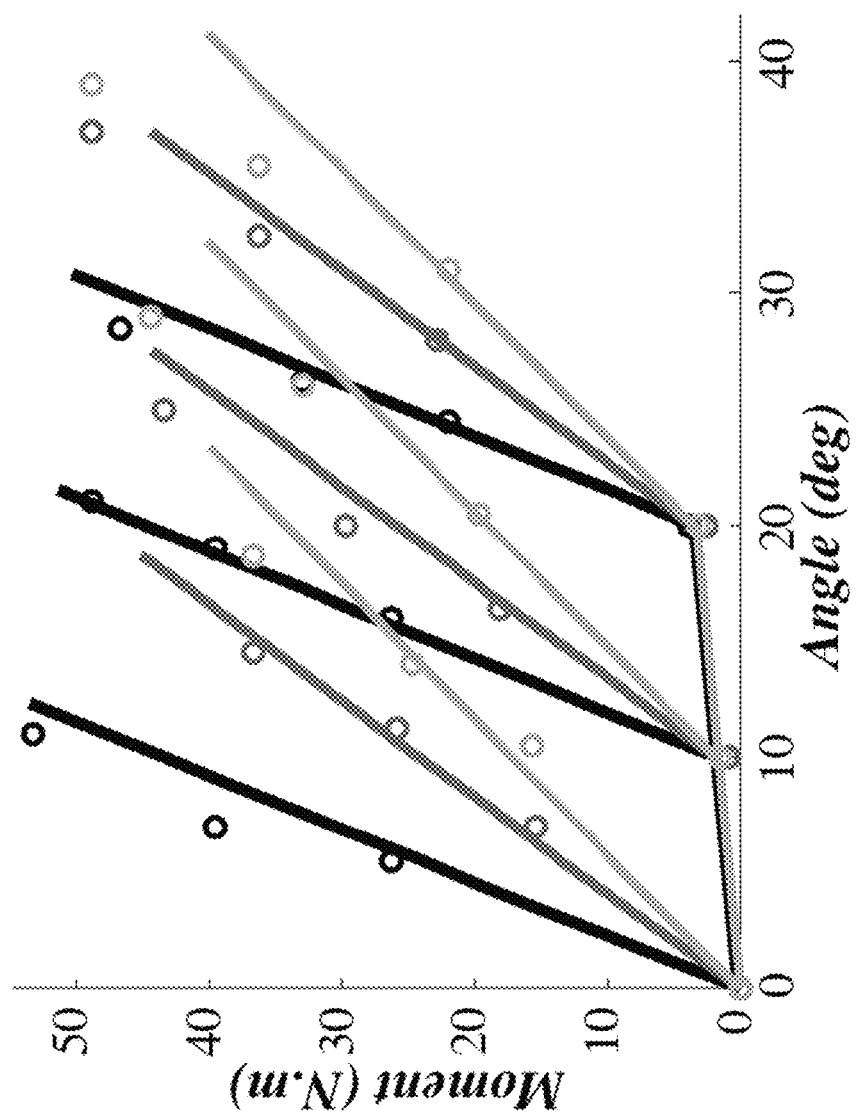
FIG. 25 is a moment-angle characterization of the compliant stance control module using three different support springs: 239 N·m·rad-$^1$ shown by black, 127 N·m·rad-$^1$ shown by dark gray, and 89 N·m·rad-$^1$ shown by light gray, and three different angle of engagement: 0, 10, and 20 deg. Experimental data are shown with circles and the theoretical data with solid lines. The stiffness of the return spring is 13 N·m·rad-$^1$.

Applicants measured the moment-angle performance of the device and the maximum moment that the device can hold. Applicants mounted the CSCM on a test bench and applied a series of moments under three levels of stiffness and three angles of engagement. For each condition, Applicants recorded the flexion angle at which the CSCM was stabilized. FIG. 25 shows the results of the experiment wherein the device employed a return spring with linear stiffness of 5 N·mm$^{-1}$ (equivalent to 13 N·m·rad$^{-1}$), and support springs with linear stiffnesses of: a. 92 N·mm$^{-1}$ (equivalent to 239 N·m·rad$^{-1}$), b. 42 N·mm$^{-1}$ (equivalent to 127 N·m·rad$^{-1}$), and c. 34 N·mm$^{-1}$ (equivalent to 89 N·m·rad$^{-1}$). The moment-angle data for conditions a, b, and c are shown with black, dark gray, and light gray, respectively. The experimental data are shown with circles and the theoretical data suggested by equation (6) with solid lines. FIG. 25 shows that equation (6) closely explains the moment-angle performance of the CSCM, especially at the low knee flexion values usually observed in walking. As dictated by the design objectives, Applicants also applied moments of up to 110 N·m on the CSCM and found it able to tolerate them and hold its latch. The CSCM also functioned properly when the support spring was replaced with a solid cylinder (i.e. "rigid" joint).

Preclinical Dynamic Loading

Figure 26:
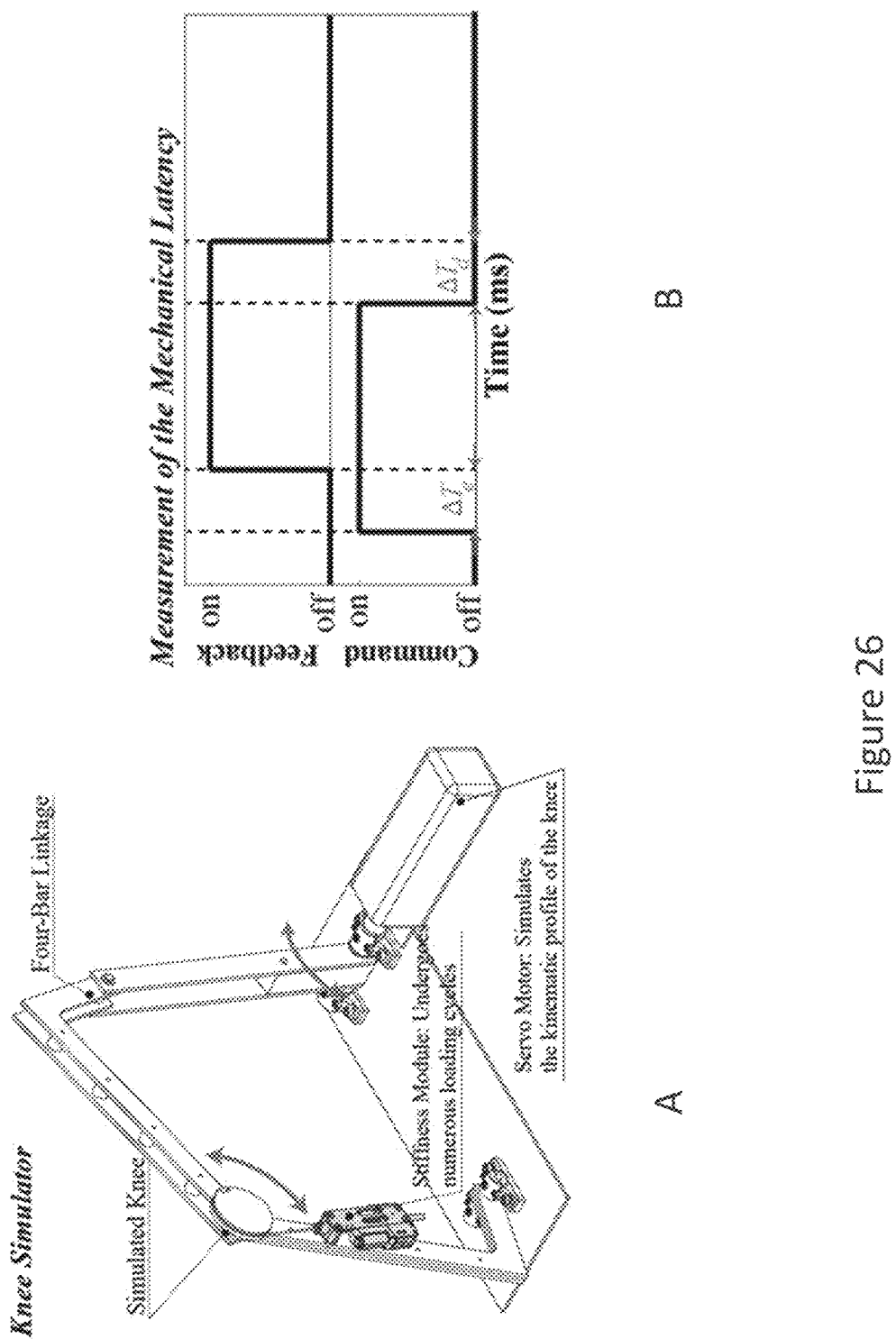
FIG. 26 shows the knee simulator used to evaluate the mechanical function of the compliance control module and to measure the spring engagement/disengagement latency (A). The simulator is primarily a four-bar linkage mechanism driven by a servo motor. The compliance control module is mounted on the device and undergoes numerous working cycles. (B): The simulator controller sends an engagement command signal to the compliance control module and receives the feedback from the pushbuttons embedded in the module. The time differences between these signals indicate the mechanism engagement/disengagement latency.

Applicants fabricated a mechanical knee simulator in order to evaluate the reliability and measure the latency of the CCM, as schematically shown in FIG. 26-A. The test machine consists of a four-bar linkage actuated by a large 3-phase servomotor and servo controller (SGMAV-10A3A61 from Yaskawa and SGDV120AE from Omron Companies). The servomotor follows the kinematic profile of the joint for which the module is being designed (here, the knee joint angle profile, taken from normative subject data). The controller also sends a digital signal to the CCM to engage the support spring during the simulated stance phase and disengage during the rest of the gait, as shown in FIG. 26-B. The setup also records the feedback signals from the push-buttons embedded in the CCM to identify when the engagement/disengagement actually occurs. As discussed earlier, the mechanical system of the CCM imposes latency on the engagement/disengagement. The engagement latency ($\Delta T_e$) and disengagement latency ($\Delta T_d$) were estimated by measuring the time period between the command and feedback signals. Applicants fabricated a prototype of the CCM and tested it on the knee joint simulator as schematically shown in FIG. 26-A. The prototype successfully underwent ~30,000 gait cycles (with maximum moment of 60 Nm/rad) without any failure in the mechanical components and engagement. The average latencies for both engagement and disengagement were also measured using the test machine and reported to be ~30 ms.

Preliminary Human Subjects Tests

Applicants conducted a preliminary test on three healthy volunteers according to experimental protocols approved by the Institutional Review Board of Yale University. FIG. 27 includes the demographic data of the volunteers as well as the preferred gait speeds of the trials. Applicants compared the inter-subject mean kinematic profiles of the hip, knee, and ankle of the volunteers under compliant support provided by the CSCO with the rigid support provided by a SensorWalk commercial SCKAFO (OttoBock), which is likely the most advanced commercialized stance control orthosis. This device contains an electromechanical clutch at the knee that engages to lock the knee joint during the stance phase (sensed through an insole-based sensor), and releases the knee during swing.

Figure 28:
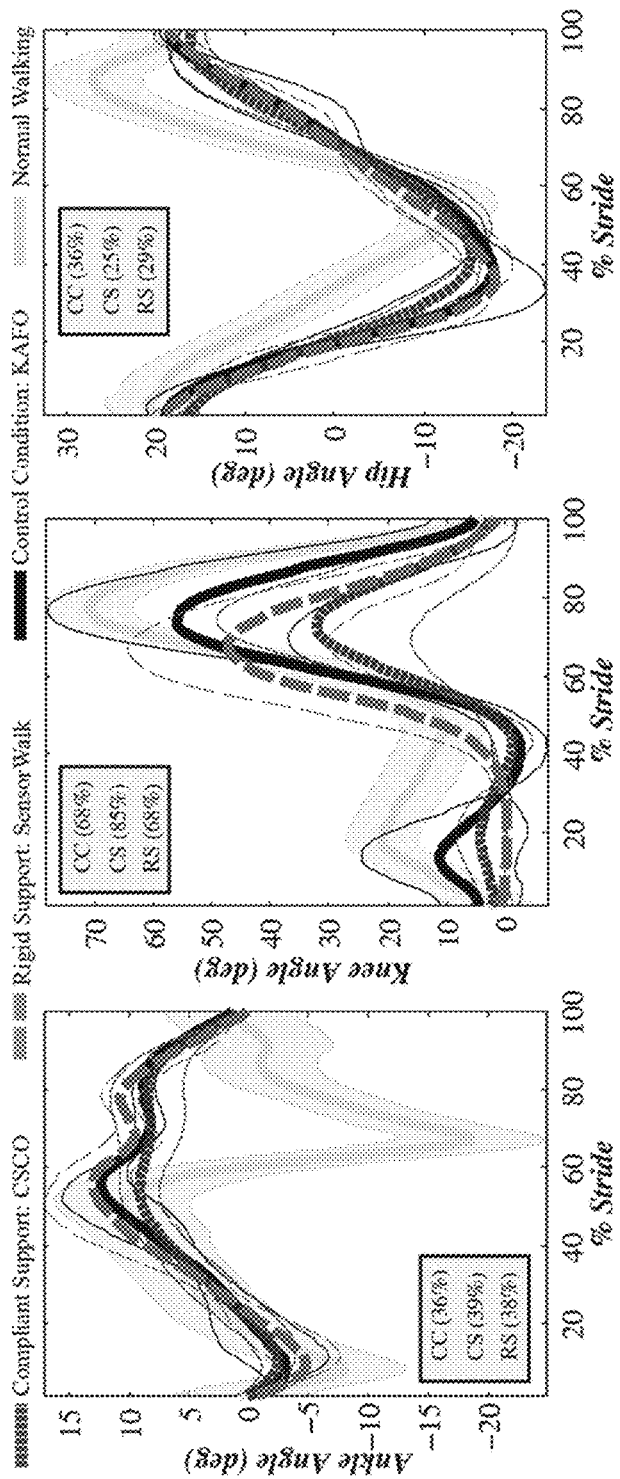
FIG. 28 are graphs depicting inter-subject mean angle profiles of the ankle, knee, and hip joints for three healthy volunteers walking at the preferred gait speed on a treadmill. Compliant Support (CS): Volunteers walking with the CSCO with support spring stiffness of 240 N·m·rad-$^1$, shown by black. Rigid Support (RS): Volunteers walking with SensorWalk representing current stance control orthosis, shown by dark gray, and Control Condition (CC): Volunteers walking with the KAFO of SensorWalk/CSCO, shown by light gray. The figure also includes the normative angle profiles observed in average humans in normal walking. The thin lines show one standard deviation above and below the graphs.

The experiment included three conditions each consisting of 10 minutes of walking at the preferred gait speed according to the feedback obtained from the volunteers: a. Control Condition (CC), b. Rigid Support (RS), and c. Compliant Support (CS). All conditions involved the device on the right leg of the volunteers, with no device on the left leg. The control condition consisted of the volunteers walking with a carbon-fiber jointed KAFO (i.e. free-swinging "pin" joint) without an active control module (the stance control modules of the SensorWalk and CSCO were assembled on the same KAFO, custom fit to the volunteers by a professional orthotist and fabricated by Otto Bock). The rigid support condition consisted of the volunteers walking with the SensorWalk device. For the compliant support condition, Applicants replaced the stance control module of the SensorWalk with the CSCM. The equivalent support spring and return spring stiffnesses of the CSCM were chosen to be 240 N·m·rad$^{-1}$ and 2 N·m·rad$^{-1}$, respectively. To measure the joint angles, Applicants placed a potentiometer at the knee and ankle of the devices and an instrumented orthopaedic goniometer (a potentiometer integrated in a goniometer from Elite Medical Instruments) at the hip joint of the volunteers. FIG. 28 illustrates the graphs of the inter-subject mean angles of hip, knee, and ankle by thicker traces as well as the lower and upper boundaries defined by the standard deviations with thinner traces. In this figure, black represents the results achieved by the CSCO, dark gray by the SensorWalk, and light gray by the jointed passive KAFO. The right heel strikes identified the beginning of the gait cycles. To give a sense of the repeatability of the traces over the entire gait period, the coefficients of variability (CV) of the mean profiles are also reported on each graph.

In order to compare the two Stance-Control Orthosis conditions (CSCO and SensorWalk), Applicants calculated the common variance of correlation ($R^2$) and f-test p-value (p) between the joint angles when walking with those devices and when walking with the passive, jointed KAFO (control condition). Applicants found $R^2$ values of 98%, 70%, and 98% for the ankle, knee, and hip angles, respectively, when walking with the SensorWalk, and $R^2$ values of 97%, 97%, and 98% when walking with the CSCO compared to walking with the KAFO as the baseline, with p<0.0001 for all profiles. Considering those values, the performance of the CSCO is closer to the control condition than the Sensor Walk, and especially so for the knee joint. These similarities and differences can also be qualitatively seen in the traces in FIG. 28.

Figure 29:
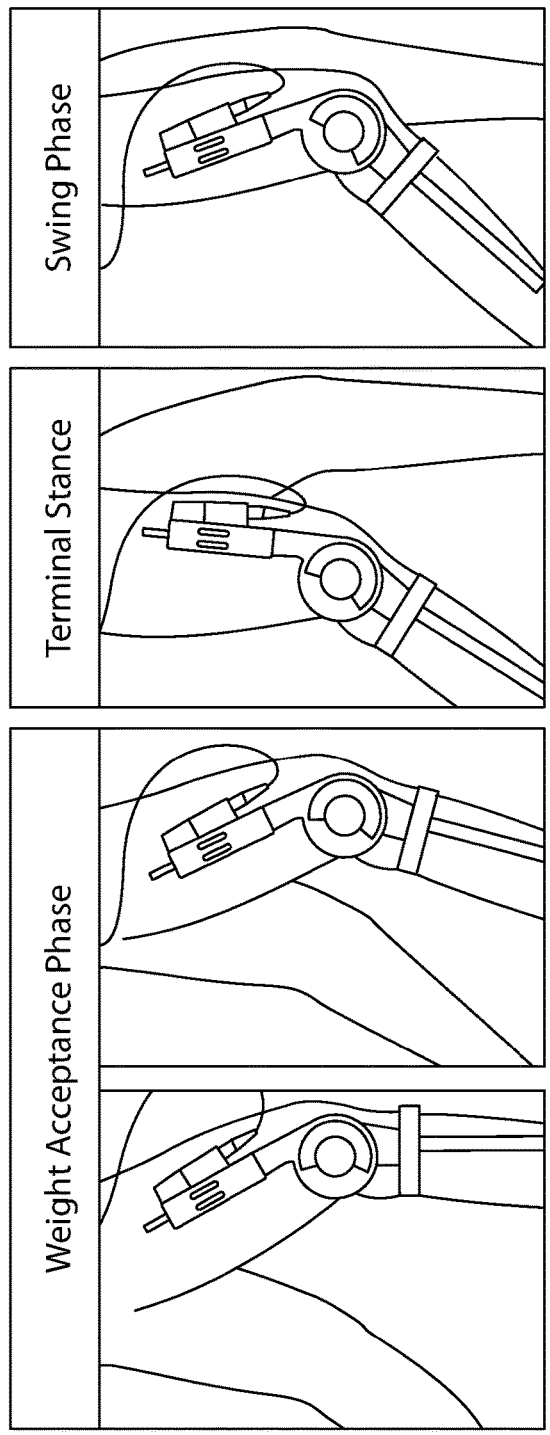
FIG. 29 depicts high-speed image captures of the compliant stance control orthosis in a gait cycle of a healthy subject walking on a treadmill. The device compliantly supports the knee during the weight acceptance phase and liberates it during the rest of the gait.

As additional measures, Applicants reported the preferred gait speed of the volunteers across all conditions. Applicants found an average preferred speed of ~0.93 ms-1 for the control and compliant support conditions, and ~0.83 ms-1 for the rigid support condition, as reported in FIG. 27. A sequence of high-speed image captures of the treadmill gait of one of the volunteers is also shown in FIG. 29.

Presented in this example is the mechanical design and functional evaluation of a quasi-passive compliant stance control orthosis (CSCO) that can compliantly support the impaired or weak knee joint of a patient suffering from musculoskeletal disorders when walking on level ground. Inspired by the natural behavior of healthy human knees, the CSCO implements a spring in parallel with the knee joint to fully/partially replace the function of quadriceps in the stance phase, and liberates the knee joint in the swing phase to allow for free progression of the leg to initiate the next step. As described herein, the control algorithm was developed to identify the gait phase and determine the engagement/disengagement of the orthosis support spring.

The three experiments of Example 2 Applicants conducted to ensure that the CSCO demonstrates proper reliability, latency, and durability, and also to ensure that the CSCO does not substantially affect gait kinematics. In the first set of tests, Applicants applied static moments on the compliant stance control module (CSCM) of the CSCO and observed that the moment-angle behavior of the CSCM validates the theoretical characterization of the device. In the second set of tests, Applicants evaluated the reliability, latency, and endurance of the CSCO on a testing machine over more than 30,000 working cycles. Finally, Applicants conducted a preliminary human subjects test on three healthy volunteers using the CSCO, SensorWalk, and a control condition using the KAFO of the CSCO/SensorWalk. It was found that the kinematic patterns of the volunteers remained relatively invariant during walking with the CSCO and relatively variant with SensorWalk, in comparison to those of the volunteers during walking with the KAFO as the baseline.

The design of the CSCO is based on the hypothesis that compliant support can be beneficial to subjects with an unimpaired hip and an impaired knee. Experiments show that the CSCO may also provide biomechanical benefits to healthy subjects, enable higher gait speed, longer walking distance/period, and lower energy expenditure compared with current SCKAFOs.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. An impedance modulation device for an orthotic application, comprising:
    a high-stiffness loading spring having a first spring constant;
    a low-stiffness return spring having a second spring constant lower than the first spring constant;
    a shaft having an output connector;
    an engagement mechanism comprising a gear, an actuator that drives the gear, and a lever configured to be pushed by the gear; and
    a bearing block configured to latch and unlatch to the shaft;
    wherein when the engagement mechanism engages the shaft to latch the bearing block to the shaft, the device exhibits a high stiffness at the output connector, and wherein when the engagement mechanism disengages the shaft to unlatch the bearing block to the shaft, the device exhibits a low stiffness at the output connector.

2. The device of claim 1, wherein a portion of the shaft along its length passes through a hole in the lever.

3. The device of claim 2, wherein the engagement mechanism engages the shaft by pushing the lever into contact with the shaft.

4. The device of claim 1, wherein at least a portion of the low-stiffness return spring is positioned at least partially within the core of the high-stiffness spring.

5. The device of claim 4, wherein at least a portion of the shaft is positioned at least partially within the core of the low-stiffness return spring.

6. An orthotic device, comprising:
a frame;
an impedance modulator comprising:
- a high-stiffness loading spring having a first spring constant,
- a low-stiffness return spring having a second spring constant lower than the first spring constant,
- a shaft having a connector, and
- an engagement mechanism comprising a gear, an actuator that drives the gear, and a lever configured to be pushed by the gear, and;
- a bearing block; and a pulley assembly positioned relative to a joint and connected to the shaft connector;
wherein the pulley assembly turns and pulls the shaft of the impedance modulator, and when the engagement mechanism engages the shaft to latch the bearing block to the shaft, the impedance modulator exhibits a high stiffness at the shaft connector, and when the engagement mechanism disengages the shaft to unlatch the bearing block to the shaft, the impedance modulator exhibits a low stiffness at the shaft connector.

7. The orthotic device of claim 6, wherein the device is a knee-ankle-foot-orthosis.

8. The orthotic device of claim 7, further comprising a controller.

9. The orthotic device of claim 8, wherein the controller detects if a foot portion of the knee-ankle-foot-orthosis is in contact with the ground or is off the ground, and wherein when the foot portion of the knee-ankle-foot-orthosis is on the ground, the modulator exhibits high stiffness, and when the foot portion of the knee-ankle-foot-orthosis is off the ground, the modulator exhibits low stiffness.

10. The orthotic device of claim 6, further comprising a brushless or brushed motor and a harmonic drive gear.

11. The orthotic device of claim 6, wherein a portion of the shaft along its length passes through a hole in the lever.

12. The orthotic device of claim 11, wherein the engagement mechanism engages the shaft by pushing the lever into contact with the shaft.

* * * * *